(12) United States Patent
Robinson

(10) Patent No.: US 6,278,889 B1
(45) Date of Patent: Aug. 21, 2001

(54) ROBUST ACCURATE NON-INVASIVE ANALYTE MONITOR

(76) Inventor: Mark R. Robinson, 1603 Solano NE., Albuquerque, NM (US) 87110

( * ) Notice: Subject to any disclaimer, the term of this patent is extended or adjusted under 35 U.S.C. 154(b) by 0 days.

(21) Appl. No.: 09/410,193

(22) Filed: Sep. 30, 1999

Related U.S. Application Data

(63) Continuation of application No. 09/082,362, filed on May 20, 1998, now abandoned, which is a continuation of application No. 08/794,677, filed on Feb. 3, 1997, now Pat. No. 5,830,132, which is a continuation of application No. 08/111,377, filed on Aug. 24, 1993, now abandoned.

(51) Int. Cl.$^7$ ........................................... A61B 5/00
(52) U.S. Cl. ............................ 600/322; 600/323
(58) Field of Search ................... 600/322, 323, 600/310; 356/41

(56) References Cited

U.S. PATENT DOCUMENTS

| 4,570,638 | 2/1986 | Stoddart et al. . |
| 4,655,225 | 4/1987 | Dahne et al. . |
| 4,768,516 | 9/1988 | Stoddart et al. . |

(List continued on next page.)

OTHER PUBLICATIONS

"Post–Prandial Blood Glucose Determination by Quantitative Mid–Infrared Spectroscopy," K.J. Ward, et al., *Applied Spectroscopy*, vol. 46, No. 6, 1992, pp. 959–965.

"Reagentless Near–Infrared Determination of Glucose in Whole Blood Using Multivariate Calibration," David M. Haaland, et al., *Applied Spectroscopy*, vol. 46, No. 10, 1992, pp. 1575–1578.

"Noninvasive Glucose Monitoring in Diabetic Patients: A Preliminary Evaluation," M. Ries Robinson, et al., *Clinical Chemistry*, vol. 38, No. 9, 1992, pp. 1618–1621.

"Near–IR Fiber–Optic Probe for Electrolytes in Aqueous Solution," Jie Lin, et al., *Analytical Chemistry*, vol. 65, No. 3, Feb. 1, 1993, pp. 287–292.

(List continued on next page.)

*Primary Examiner*—Robert L. Nasser
(74) *Attorney, Agent, or Firm*—DeWitt M. Morgan

(57) ABSTRACT

An improved method and apparatus for determining noninvasively and in vivo one or more unknown values of a known characteristic, particularly the concentration of an analyte in human tissue. The method includes: (1) irradiating the tissue with infrared energy (400 nm–2400 nm) having at least several wavelengths in a given range of wavelengths so that there is differential absorption of at least some of the wavelengths by the tissue as a function of the wavelengths and the known characteristic, the differential absorption causeing intensity variations of the wavelengths incident from the tissue; (2) providing a first path through the tissue; (3) optimizing the first path for a first sub-region of the range of wavelengths to maximize the differential absorption by at least some of the wavelengths in the first sub-region; (4) providing a second path through the tissue; and (5) optimizing the second path for a second sub-region of the range, to maximize the differential absorption by at least some of the wavelengths in the second sub-region. In the preferred embodiment a third path through the tissue is provided for, which path is optimized for a third sub-region of the range. With this arrangement, spectral variations which are the result of tissue differences (e.g., melanin and temperature) can be reduced. At least one of the paths represents a partial transmission path through the tissue. This partial transmission path may pass through the nail of a finger once and, preferably, twice. Also included are apparatus for: (1) reducing the arterial pulsations within the tissue; and (2) maximizing the blood content in the tissue.

14 Claims, 34 Drawing Sheets

U.S. PATENT DOCUMENTS

| | | |
|---|---|---|
| 4,867,165 | 9/1989 | Noller et al. . |
| 4,880,304 | 11/1989 | Jaeb et al. . |
| 4,883,963 | 11/1989 | Kemeny et al. . |
| 5,028,787 | 7/1991 | Rosenthal et al. . |
| 5,057,695 | 10/1991 | Hirao et al. . |
| 5,077,476 | 12/1991 | Rosenthal . |
| 5,111,817 | 5/1992 | Clark et al. . |
| 5,120,961 | 6/1992 | Levin et al. . |
| 5,139,025 | 8/1992 | Lewis et al. . |
| 5,158,082 | 10/1992 | Jones . |
| 5,188,108 | 2/1993 | Secker . |
| 5,222,496 | 6/1993 | Clarke et al. . |
| 5,370,114 | 12/1994 | Wong et al. . |

OTHER PUBLICATIONS

"The Optics of Human Skin," R. Rox Anderson, et al., *The Journal of Investigative Dermatology*, vol. 77, No. 1, Jul. 1981, pp. 13–19.

"Acousto–Optic Devices, Optical Elements for Spectroscopy," Chieu D. Tran, *Analytical Chemistry*, vol. 64, No. 20, Oct. 15, 1992, pp. 971A–918A.

"Defense–Related Acousto–Optics Transform Commercial Products," Ronald G. Rosemeier, *Photonics Spectra*, Jan. 1993, pp. 83–84.

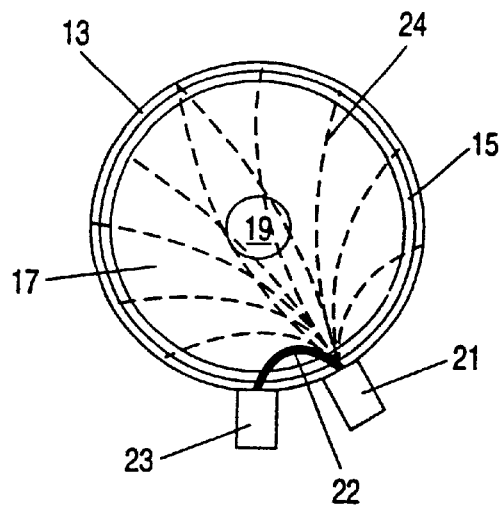
FIG 9A
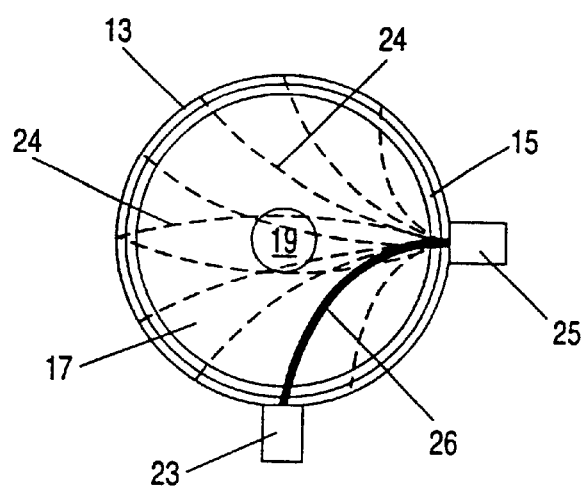
FIG 9B
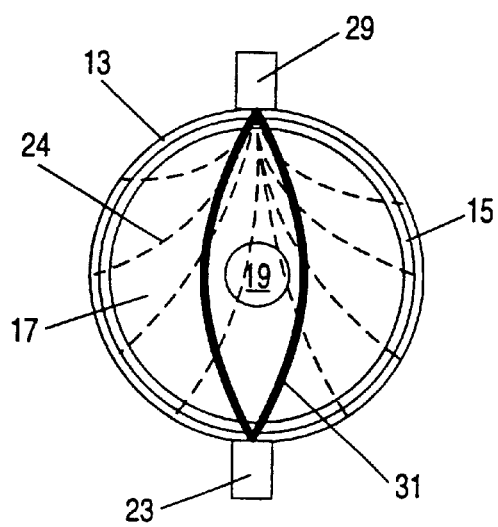
FIG 9C
FIG 9

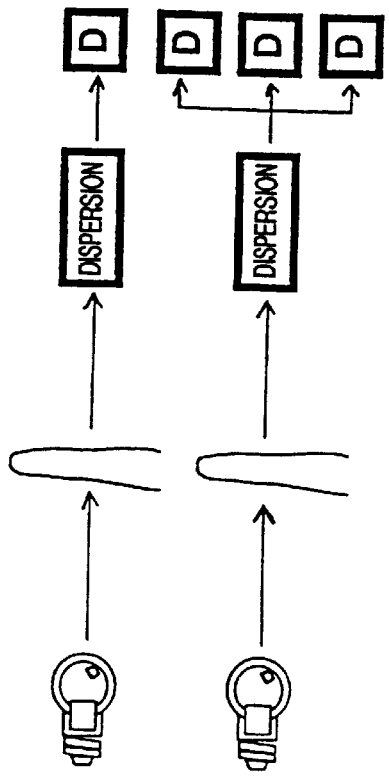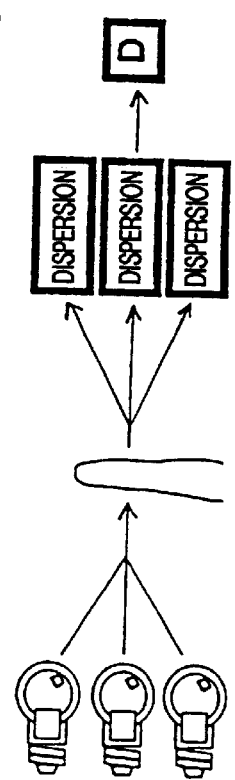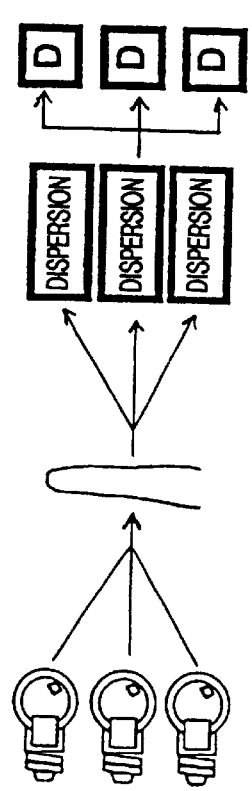
FIG-31

ROBUST ACCURATE NON-INVASIVE ANALYTE MONITOR

This is a continuation of application Ser. No. 09/082,362 filed on May 20, 1998, now abandoned, which is a continuation of application Ser. No. 08/794,677 filed on Feb. 3, 1997 (now U.S. Pat. No. 5,830,132) which is a continuation of application Ser. No. 08/111,377 filed on Aug. 24, 1993 (now abandoned).

FIELD OF THE INVENTION

The present invention relates to a robust, accurate noninvasive analyte monitor, particularly to a reliable instrument (and associated methodology) for the measurement of glucose levels in a human in both clinical and at home situations. Other analytes which can also be measured include alcohol, BUN (blood urea nitrogen), bilirubin, hemoglobin, creatine, cholesterol, and electrolytes.

BACKGROUND OF THE INVENTION

A major limitation to the clinical goal of achieving ideal diabetic glucose control is the unavailability of unlimited and/or continuous glucose monitoring. Despite the noninvasive advances described in U.S. Pat. No. 4,975,581 to Robinson, et al., a lancet cut into the finger is still necessary for all present forms of home glucose monitoring. This is so compromising to the diabetic patient that the most effective use of any form of diabetic management is rarely achieved, including multiple insulin shots, continuous subcutaneous pump delivery, intraperitoneal or intravascular implanted pump delivery, or oral diabetic pharmaceutical agents. It is possible that diabetic glycemia could be controlled with conventional treatment, external pumps, or implanted insulin delivery devices, if on-line or continuous glucose levels were known by the patient or by a monitoring system. Such information would enable development of a closed loop insulin delivery system.

The theoretical basis for non-invasive glucose determination is based upon quantitative infrared spectroscopy. Infrared spectroscopy measures the electromagnetic radiation (0.7–25 $\mu$m) a substance absorbs at various wavelengths. Molecules do not maintain fixed positions with respect to each other but vibrate back and forth about an average distance. Absorption of light at the appropriate energy causes the molecule to become excited to a higher vibrational level. The excitation of the molecule to an excited state occurs only at certain discrete energy levels, which are characteristic for that particular molecule. Most primary vibrational states occur in the mid-infrared frequency region (i.e., 2.5–25 $\mu$m). However, noninvasive analyte determination in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determination at these wavelengths. Overtones of the primary vibrations occur at ½, ⅓, ¼... and so on of the wavelength of the fundamental mode. Additionally, combination bands also exist. A combination band occurs when the radiation has the correct energy to excite two vibrations at once.

Although glucose absorbs at multiple frequencies in both the mid and near infrared, there are other infrared active analytes in the blood which also absorb at similar frequencies. Due to the overlapping nature of these absorption bands no single or specific frequency can be used for reliable noninvasive glucose measurement. Analysis of spectral data for glucose measurement thus requires evaluation of many spectral intensities over a wide spectral range to achieve the sensitivity, precision, accuracy, and reliability necessary for quantitative determination. This is also true for other blood analytes. In addition to overlapping absorption bands, measurement of glucose is further complicated by the fact that glucose is a minor component by weight in blood and that the resulting spectral data may exhibit a nonlinear response due to both the properties of the substance being examined and/or inherent nonlinearities in optical instrumentation.

The difficulty of modeling the spectral response requires, as set forth in U.S. Pat. No. 4,975,581, the use of multivariate statistical methods rather than univariate methods. These techniques allow information to be extracted from data which cannot be obtained by other data analysis routines. The methods previously disclosed in U.S. Pat. No. 4,975,581, increase analytical precision to the point where the spectroscopic methods become useful for clinical determinations.

Using expensive optical instrumentation, the technology disclosed in U.S. Pat. No. 4,975,581 has been applied for the quantitative measurement of analytes in biological fluids. The focus of this effort has been in the area of noninvasive glucose measurement, portions of which are described in: (1) "Post-Prandial Blood Glucose Determination by Quantitative Mid-Infrared Spectroscopy", K. J. Ward, D. M. Haaland, M. R. Robinson and R. P. Eaton, *Applied Spectroscopy*, Vol. 46, No. 6, 1992, pages 959–965, (2) "Reagentless Near-Infrared Determination of Glucose In Whole Blood Using Multivariate Calibration", D. M. Haaland, M. R. Robinson, G. W. Koepp, E. V. Thomas, and R. P. Eaton, *Applied Spectroscopy*, Vol. 46, No. 10, 1992, pages 1575–1578, and (3) "Noninvasive Glucose Monitoring in Diabetic Patients: a Preliminary Evaluation", M. R. Robinson, R. P. Eaton, D. M. Haaland, G. W. Koepp, E. V. Thomas, B. R. Stallard and P. L. Robinson, *Clinical Chemistry*, Vol. 38, No. 9, 1992, pages 1618–1622.

In addition to the body of glucose research disclosed by the foregoing papers, M. K. Alam, R. P. Eaton, D. M. Haaland, M. R. Robinson, P. L. Robinson and E. V. Thomas (hereinafter Alam, et. al.) have worked extensively in the near infrared from 700 to 1400 nm. This spectral region allows transmission of the infrared light through the finger and contains meaningful glucose information. With type-I diabetic volunteers, three representative instrument configurations were investigated. In the first, as disclosed in *Clinical Chemistry*, Vol. 38, No. 9, a Nicolet 800 FTIR instrument equipped with a InSb detector was used. The second system utilized a SPEX grating spectrometer equipped with a germanium array detector. In the third configuration, the SPEX grating spectrometer equipped with the germanium array detector was coupled with fiber optics, which transmitted the light from the instrument to the finger and from the finger back to the instrument. The clinical protocol and method for evaluation of IR spectroscopy for the in vitro determination of blood glucose is described in more detail in the above identified patent and published papers. Work on the second and third configurations has not been published.

With a Nicolet 800 Fourier transform infrared spectrometer (FTIR) equipped with an InSb detector, a diabetic patient undergoing a meal tolerance test was examined using near-infrared transmission measurements through his finger. The patient's blood glucose levels varied between 48 mg/dl and 481 mg/dl, with 41 samples obtained. The average absolute error of prediction on all samples was 19.8 mg/dl. The data are plotted in FIG. 1.

The feasibility of non-invasive glucose determination was next investigated on a grating spectrometer equipped with a germanium array detector. The optical sampling method was transmission of light (800–1330 nm) through the patient's index finger. The patient's blood glucose level varied between 92 mg/dl and 434 mg/dl, with 29 samples obtained. The average absolute error of prediction for this data was approximately 24.3 mg/dl. The data are plotted in FIG. 2.

In the final instrument configuration, the grating spectrometer-germanium detector instrument was outfitted with a fiber optic sampling configuration. Fiber optics were used both to transmit light to the finger and to collect light from the opposite side of the finger. The patient's blood glucose level varied from 83 mg/dl and 399 mg/dl, with 21 samples obtained. Analysis of the data yielded an average absolute error of 11.9 mg/dl. The data are plotted in FIG. 3. The accuracy of this non-invasive determination is comparable to the accuracy of existing invasive home glucose monitors. The results from the fiber optic study were, vis-a-vis the first two configurations, improved due to the ability to repeatedly position the finger between the fiber bundles. Repeatable positioning of the finger decreased the baseline variation observed in the spectra and, it is believed, improved the accuracy of the noninvasive prediction.

In all the above studies, the sampling apparatus used consisted of a circular tube which matched the approximate size of the patients' fingers. The light entered the finger on the palmar side and exited through the fingernail. Although clinically useful measurements were made, the finger sampling techniques used and the instrumentation employed during these studies are not optimal, extremely expensive, and not suitable for either clinical or home use. Thus, improvements in both areas are required before a device can be made available for use by the diabetic patient.

In general, the sampling device should perform two major functions:
1. Enable maximal procurement of spectral information for measurement of the analyte of interest; and
2. Minimize those spectral variations associated with sampling the tissue that adversely influence the quantitative measurement of the analyte.

The following specific inadequacies have been identified in prior art sampling devices:
1. The sampling apparatus utilized does not allow measurement of any wavelengths containing glucose information in the 1400 to 2400 nm region;
2. The sampling apparatus does not optimize sampling geometry for the light propagation characteristics of the wavelengths to be measured;
3. There is no compensation for the influence of skin pigmentation differences between patients;
4. The finger sampling apparatus utilized does not allow repeated sampling of a single patient's finger and does not minimize between patient differences;
5. There is no compensation for the influence of arterial pulsations in patients' tissue (e.g., finger); and
6. The sampling device is not temperature controlled.

To understand the inadequacies of the current sampling device and associated instrumentation, and to recognize the benefits of the disclosed invention, a general understanding of infrared spectroscopy and of light propagation characteristics in tissue is necessary.

Spectroscopic information which facilitates the measurement of glucose occurs over the majority of the near infrared region. In those wavelength regions suitable for noninvasive measurement glucose has absorption peaks in the following areas: 950–1050 nm; 1150–1300 nm; 1510–1850 nm; and 2070–2370 nm. If correctly processed, the judicious use of spectroscopic information from the entire wavelength region will yield better quantitative results than only one wavelength region. The utility of using all possible information is especially true in complex environments such as human tissue.

To demonstrate the utility of using multiple wavelength regions a simple experiment was performed. A set of cuvette samples containing water, urea, and glucose were optically sampled over the entire wavelength region from 700 to 2400 nm. The optical pathlength used for data acquisition was 1 cm in the 700 to 1400 nm range and 1 mm in the 1400 to 2400 nm range. The change in pathlength was necessitated due to differences in the absorbance of water in given wavelength regions, the importance of which is discussed at length in the Description of the Preferred Embodiments. The resulting spectra was processed using four different wavelength ranges. The results are shown in Table I below.

TABLE I

| Wavelength Region | # of wavelengths used in 700–1100 nm | # of wavelengths used in 1100–1400 nm | # of wavelengths used in 1400–2000 nm | # of wavelengths used in 2000–2400 nm | Total number of wavelengths used | Standard error of prediction |
| --- | --- | --- | --- | --- | --- | --- |
| 700–1100 nm | 7 | N/A | N/A | N/A | 7 | 18.1 |
| 700–1400 nm | 6 | 2 | N/A | N/A | 8 | 12.2 |
| 700–2000 nm | 4 | 4 | 6 | N/A | 14 | 10.4 |
| 700–2400 nm | 3 | 7 | 8 | 5 | 23 | 5.83 |

Thus, it is clear that the inclusion of information from all wavelength regions containing glucose information improves the accuracy of the optical measurement. Therefore, it is an object of the present invention to provide for a tissue sampling device and associated instrumentation which enables use of spectral information from, in the case of glucose, the entire wavelength region from 700 to 2400 nm.

In order to access the entire wavelength region from 700 to 2400 nm, the light propagation characteristics in tissue at these wavelengths must be understood. Although multiple papers have been published on the optical properties of skin, literature on the optical properties of the entire finger is sparse. The finger is a complex, dynamic, variable, heterogenous and multilayered optical media, which makes entirely rigorous analysis difficult. As light enters the finger it undergoes multiple and diverse scattering effects throughout its tortuous path of propagation. The overall optical response is a combination involving molecular (Rayleigh) scattering, particle (Mie) scattering, and index (Fresnel and Christiansen effect) scattering. A simplistic diagram of the light propagation characteristics of light within the body is schematically illustrated in FIG. 1 of "The Optics of Human Skin", R. Rox Anderson, B. S. and John A. Parrish, M. D., *The Journal of Investigative Dermatology,* 77:13–19, 1981. For convenience, a slightly modified version is illustrated in FIG. 4. The light entering the tissue is either absorbed, reflected or transmitted. Transmission is defined as that fraction of the radiation incident on one side of the sample that passes through the sample. A second type of optical sampling, "partial transmission" (sometimes referred to as "diffuse reflectance"), is defined as that fraction of light that interacts with the tissue and where the sampling does not require location of the source and detector on opposite sides of the body part. See FIG. 4. "Simple reflectance" is defined as that fraction of radiation incident upon one side that returns directly from the surface of the sample. The information content of this reflected light is negligible as the light is reflected by the bloodless epidermis.

The optical characteristics of the epidermis and dermis are well characterized. Over the region from 400 to 1300 nm, the skin can be modeled by considering the thin epidermis to be an optically absorbing element with negligible scattering, overlying the thick dermis, which acts as a diffuse reflector. Transmission through the epidermis is mainly a function of melanin, which resides solely in the epidermis. The transmission characteristics of the dermal element depends upon both scattering mainly by collagen and absorption. It is important to note that in both transmission and partial transmission the light must transverse the melanin containing epidermis twice. Returning to FIG. 4, it will be seen that light penetrates the epidermis, interacts with the dermis, and will eventually interact with subcutaneous tissues. The capillary bed below the epidermis is the most superficial vascular layer and light propagation to this level or deeper is desired for reliable non-invasive analyte determination. Thus, light having transversed this region will contain the necessary spectral information for analyte measurement (e.g., alcohol, cholesterol, BUN (blood urea nitrogen), creatine, hemoglobin and bilirubin).

As previously demonstrated the use of information from all wavelength regions improves both the sensitivity and specificity of the optical measurement. However, transmission measurements through the finger become problematic at wavelengths greater than 1400 nm due to the absorbance of the radiation by water. Water peaks are seen at 760, 1000, 1200, 1450, and 2000 nm, with each associated band exhibiting a marked increase in absorption. See "Near-infrared Studies of the Structure of Water. I. Pure Water", Buijs, K. and Choppin, G. R., *Journal of Chemical Physics,* Vol. 39, No. 8, October 1965. The human body is approximately 70% water and in the near infrared spectral region water is the largest absorber. When considering the finger, it can be simplistically modeled as a highly scattering aqueous media surrounded by skin. FIG. 5 shows a simplified model of a finger/thumb 11, which can be grossly modelled as a water cuvette having a pathlength of 1 cm. Finger/thumb 11 includes epidermis 13, dermis 15, the subcutaneous tissue 17 and bone 19. FIG. 6 shows the absorbance of water versus wavelength for a 1 mm pathlength on the right hand axis and shows relative pathlength versus wavelength on the left hand axis. Although influenced by the intensity of the light source, the relative pathlength on the y-axis corresponds to a unit absorbance of one at the x-axis wavelength location. Examination of FIG. 6 reveals that transmission measurements through the finger are difficult at wavelengths of greater than 1400 nm using a standard tungsten halogen lamp due to limitations in light propagation. These concepts concerning optical transmission characteristics in water are also shown in FIG. 11 of U.S. Pat. No. 4,570,638. Note, the intensity of the light source will influence the relative pathlengths at different wavelengths. The pathlengths referenced above are appropriate for a standard 100 watt tungsten halogen source.

Despite the absorbance by water, partial transmission sampling can be performed in a tissue at wavelengths greater than 1400 nm. For example, the light may enter the tissue and exit the tissue several millimeters away, as shown in FIG. 4. Thus, the light has been transmitted but only through a portion of the tissue or body part. It is an object of the present invention to use partial transmission for the procurement of spectral information at wavelengths longer than those which lend themselves to standard transmission sampling.

In quantitative spectroscopy it is desirable to maximize pathlength through the sample while maintaining an adequate signal-to-noise ratio at the detector. Thus, when making measurements in the 1000 nm region, spectral data obtained from a 1 cm cuvette will typically outperform data obtained from a 1 mm cuvette if the two sets of data have similar signal-to-noise ratios. The improved performance occurs due to the longer pathlength which forces the light to interact with the absorbing substance for a longer period of time. Thus, it is an object of the present invention to optimize the path for given wavelength regions.

The procurement of maximal spectral information can be augmented by sampling through the nail of the finger. In simplistic terms the nail provides a "window" to the highly vascular nail bed, similar to scraping away the upper layers of a person's skin and placing a glass slide on the resulting surface. This "window" is the result of the fact that optical penetration through the nail is greater than the skin, *Physical Properties of Tissue,* Chapter 3, Francis A. Duck, Academic Press 1991. Transmission differences between the nail and tissue become greater at increasing wavelength due to hydration differences between the nail and skin. As the nail has a lower water content than the skin, it facilitates spectral sampling in the longer wavelength regions.

The histological structure of the nail and nail bed further facilitates noninvasive sampling. The nail bed is defined as the area of skin covered by the nail. The epithelium of the nail bed is significantly thinner than the normal epidermis. The normal epidermis is composed of five layers: (1) stratum corneum (the outermost layer); (2) stratum lucidum; (3) stratum granulosum; (4) stratum spinosum; and (5) stratum basale (the innermost layer). The nail bed is composed of only the stratum basale and the stratum spinosum, and lacks significant keratinization. Thus, the physical distance to the highly vascular dermis is less in the nail bed. In summary, the nail is highly transmissive, has a low water content, and covers a highly vascular structure which makes optical sampling through the nail region highly desirable. The low water content of the nail is especially desirable when sampling in the 1400 to 2400 nm region. Therefore, it is an object of this invention to utilize this "window" into the body for procurement of maximal analyte information.

As the light passes through a body part such as a finger or thumb, it interacts with both tissue, intracellular fluid, and blood. As the object of the invention is to measure blood analytes, maximizing the amount of blood in the tissue being irradiated should improve the measurement. The accuracy of noninvasive measurement is determined by its correlation to standard invasive blood measurements. As the noninvasive measurement is actually a blood/tissue measurement, use of highly vascular body parts and maximization of blood content will improve measurement accuracy. The fingers and palm have much higher capillary densities than the arms, legs, or trunk, and are thus desired sampling locations.

Blood can be concentrated in the finger by several methods but venous engorgement is a method easily performed. The arterial system operates at a higher pressure than the venous system. Thus, occlusion of the venous system allows the finger to be pumped full of blood by the arterial system. The result is a finger with an above normal amount of blood (i.e., venous engorgement). However, the continued filling of the finger can cause instabilities in the optical measurement as the blood volume of the finger is changing. This change can be minimized by subsequently occluding arterial flow following proper "filling" of the finger. The result is venous engorgement of the finger which, when performed in a repeatable fashion, will enhance noninvasive analyte measurement.

The second major function of the sampling device is to minimize those spectral variations associated with sampling the finger that adversely influence the quantitative measurement of the analyte. The major problems recognized by the Applicants are: skin pigmentation differences between patients, arterial pulsations, finger thickness differences, instabilities in finger sampling, and the lack of temperature control.

Quantitative spectroscopic measurement becomes increasingly difficult as the complexity of the matrix under irridation increases. For example, FIG. 7 shows the absorbance spectra for water, glucose, alcohol and urea in the 900 to 1350 nm region. As can be seen, these substances have different absorbance characteristics, but there exist no single wavelengths where only one analyte absorbs. Spectral overlaps also exist in the wavelength region from 1350–2400 nm. Thus, the ability to isolate a single band for analyte measurement is difficult in an environment of overlapping spectral absorbencies. The degree of spectral overlap associated with noninvasive measurements is significant and any method which diminishes spectral overlap will decrease the complexity of the measurement process.

The problem of overlapping spectral absorbencies is complicated further in the wavelength region from 300 to 1100 nm due to the spectral absorbencies of melanin, bilirubin, and hemoglobin. See FIG. 8, "The Optics of Human Skin," supra. When considering the influence of overlapping spectra, the amount of overlap and the variation in the concentration of the overlapping substance are important parameters. For example, if a given substance only absorbed within a one nanometer bandwidth then omission of that wavelength would resolve the overlap problem completely. However, if the substance has a broad absorbance then omission of the wavelength region in which it absorbs is not reasonable. Thus, compensating for substances with broad spectral absorbencies is especially problematic.

In the wavelength region from 300 to 1100 nm, the optical absorbance of melanin varies significantly due to gross variations in skin pigmentation. Contrary to popular belief, melanin does not absorb light like a "neutral density" filter in the skin. Absorption by melanin decreases steadily from short wavelengths to longer wavelengths and does not have significant absorption above 1100 nm. See "The Optics of Human Skin", supra. Thus, in the wavelength region from 300 to 1100 nm melanin exhibits a broad, varying spectral influence which complicates noninvasive analyte measurement in heterogenous patient populations, especially those with varying ethnicity.

Hemoglobin is also an important absorber in the 300 to 800 nm region because its spectral influence varies as the amount of blood in a given tissue area changes. The modulation of light by pulsatile arterial flow is the fundamental principle upon which pulse oximetry is based. The amount of optical change observed due to arterial pulsations is a function of the patients' overall vascular status, heart rate and pulse pressure. As is the situation with melanin, the varying spectral absorbance of hemoglobin makes it a difficult component to model when developing multivariate calibration models. Thus, it is an object of the present invention to provide a methodology for removing these large spectral changes introduced by arterial pulsations, which do not relate to the concentration of the particular analyte of interest (e.g. glucose).

The spectral variation introduced by arterial pulsations can be minimized by understanding the physiology associated with arterial pulses. The pressure and corresponding pulse size in the arterial system near the heart is quite high. As the blood flows to the periphery and the vessels become progressively smaller both the mean pressure and pulse size decrease. As the blood enters the capillary bed the mean pressure has decreased to less than 40 mm hg and there is no longer any significant pulsatile component to the capillary blood flow. However, the light passing into and out of the tissue interacts with blood in both the pulsing arterioles and the capillary bed. The noise introduced by the pulsing arterioles can be removed by simple compression of the tissue (e.g., finger) or proximal compression of the arterial system. If one presses the finger against a sampling device, or has it compressed externally, the arterial pulsations can be minimized or removed. Thus, the simple removal of the spectral variance resulting from arterial pulsations can improve the signal-to-noise ratio of the resulting spectra, and thus improve the precision of the analyte measurement.

In addition to the foregoing problems associated with pigmentation and arterial pulsations, the quality of any noninvasive spectroscopic measurement will be improved if the sampling conditions are repeatable. In the sampling of human subjects, control of all sampling parameters becomes extremely difficult. The most significant problems identified by Alam et al. are variations in finger thickness and finger temperature.

Variation in finger thickness complicates the process of preforming noninvasive analyte measurements. In the spectroscopic literature, the majority of all quantitative spectroscopy is done with a fixed optical pathlength. In human applications such a requirement becomes impossible to satisfy. The magnitude of the problem can be reduced through the use of partial transmission sampling, often referred to as diffuse reflectance sampling. In partial transmission sampling the mean optical pathlength through the finger is determined in large part by the separation between the source and detector. The separation distance is not the sole influence on mean optical pathlength as differences in tissue composition and other physiological parameters will influence the light propagation. With reference to FIG. 4, the source and detector are on the same side of the tissue during partial transmission sampling. Due to their location on the same side of the tissue, tissue thickness has a reduced influence on the measurement. The mean optical pathlength then becomes a function of the separation between source and detector. As previously stated partial transmission sampling will reduce the spectral variation introduce by differences in tissue thickness.

The spectral variation introduced by differences in tissue temperature also complicates the noninvasive measurement of analytes. J. Lin and Cris W. Brown, "Near-IR Fiber-optic Probe for Electrolytes in Aqueous Solution", *Analytical*

*Chemistry,* Vol. 65, pages 287–292, 1993, have shown that the near infrared spectral region is sensitive to temperature effects. Marked spectral changes were observed when water solutions were subjected to temperature changes from 20° C. to 35° C. The regions most sensitive to temperature are those having extensive hydrogen bonding. These regions exhibit spectral changes as the hydrogen bonding changes with increasing temperature.

In studies by Alam et al. differences in skin temperature and its influence have been observed. In the prior articles on glucose, the sampling device (constructed of aluminum) was not temperature controlled and therefore acted as a heat sink. The result of using such an unthermostated sampling device is to change the skin temperature of the patient. As mentioned previously, any spectral influence which is broad in nature, not constant, and does not relate to glucose concentration can degrade the accuracy of the glucose measurement. At a minimum, such spectral changes increase the complexity of the multivariate calibration. The problem can be overcome or at least compensated for by thermostating the tissue and the sampling device. In the case of the finger, the average physiological temperature is approximately 82° F. with an average variation of ±5° F. The sampling device can be heated to an above normal tissue temperature to increase blood flow to the tissue area in contact with the device. The result is an increase in the vascular supply to the tissue and a corresponding increase in the blood content of the tissue. The end result of temperature regulation is a reduction in spectral variation not associated with glucose and an improvement in measurement accuracy.

In addition to problems directly associated with sampling the finger, the actual optical instrumentation discussed above is not well suited for commercial realization of a noninvasive analyte monitor. For clinical applications the spectrometer must be rugged without the need for frequent maintenance and re-calibration. Fixed grating spectrometers afford multiplex data acquisition and can be suited to the clinical environment such that maintenance and/or re-calibration are minimized. However, the accurate measurement of selected wavelengths is still a function of a precise geometrical arrangement between the grating and the detector. Vibration or mishandling can cause "blurring" of the image on the array, which translates into reduced performance. Fourier Transform spectrometers are available in the near infrared spectral region and are capable excellent resolution and sensitivity. Unfortunately since most FTIR spectrometers require precision translation of mirrors, their performance is also typically sensitive to the environment (i.e., vibrations and dust). Thus, it is highly unlikely that the instrument configurations used to demonstrate feasibility of noninvasive glucose measurement will satisfy the commercial environment.

Spectra can be generated by using multiple band-pass filters. The instruments afford high optical throughput but have limited flexibility, as a separate filter is needed for each wavelength intensity measured. Nevertheless, as disclosed in the Description of the Preferred Embodiments, filter instruments do represent a viable technology suitable for commercial realization.

The above described problems of limited stability and frequent recalibration can be addressed by using an acousto-optic tunable filter (AOTF). AOTFs are solid-state devices which utilize acousto-optic interactions in an anisotropic medium. The result is a compact solid-state spectrometer that can be tuned electronically in a matter of microseconds over a wide spectral range encompassing both the UV and IR regions. Due to its solid-state design, there are no moving parts. The AOTF is therefore immune to orientation changes and even significant shock and vibration. AOTFs are capable of excellent resolution and can be incorporated into sealed systems. The end result is a small, durable light dispersion device which allows random access to different wavelengths. See "Acousto-optic devices", Chieu D. Tran, *Analytical Chemistry,* Vol 64, No 20 Oct. 15, 1992). Also see; Photonics Global Forecast, Defense-Related Acousto-Optics Transform Commercial Products, R. G. Rosemeier, Photonics Spectra, 83–84, January, 1993; U.S. Pat. No. 4,883,963 to G. J. Kemeny et al.; and U.S. Pat. No. 5,120,961 to K. H. Levin et al.

In the operation of an AOTF, the wavelength of the diffracted light depends upon the frequency of the radio frequency (rf) signal applied to the AOTF. Light with relatively shorter wavelengths will de diffracted from the AOTF when higher rf signals are applied to the filter. For example, 514 nm light is diffracted when a 64 MHz rf signal is applied. Increasing the frequency to 75 MHz changes the diffracted wavelength to 457 nm. Thus, by simply changing the frequency of the rf signal, the operator has random access to any desired wavelength in the UV-IR region.

In addition to the previously stated characteristics, AOTFs have an additional characteristic which make them well suited for noninvasive medical instruments. The first is the ability of the AOTF to modulate the intensity of the diffracted light, (i.e. during operation the diffracted light is the light exiting the AOTF with the proper wavelength characteristics). The power of the applied rf signal can be used to control the intensity of the diffracted light. Thus, AOTFs provide a unique way to maintain the intensity of the light of different wavelengths at a desired level. By incorporating a feedback system into the AOTF driver, the power of the rf signal can be controlled and thus the intensity of light hitting the detector is controlled.

In general the preceding instruments are based on dispersion of a broadband light source with subsequent detection of the separated wavelengths. The quantitative measurement of blood analytes can be performed by the use of a discrete number of wavelengths. Specifically, glucose has been measured in vitro solutions composed of glucose, urea, alcohol and water through the use of 20 discrete groups of contiguous wavelengths. Thus, the use of sources that emit in a narrow wavelength region could be used in combination for analyte measurement. Specifically light emitting diodes (LEDs), laser diodes, or tunable lasers could be used for the noninvasive measurement of blood analytes.

As the time required to make the measurement is an important parameter, any instrument recording wavelengths in a multiplex manner is desired. The recording of more than one wavelength during a given time period will result in a multiplex advantage. Optical multiplexing increases the effective signal-to-noise ratio that can be achieved for detector-noise-limited spectroscopic measurements. For example, consider the case of measuring each wavelength intensity one at a time versus measurement of multiple wavelengths on an array detector. Given the same measurement time the signal-to-noise ratio of the array detector will exceed that of the single wavelength measurement device.

It is important to recognize that any device having either multiple detectors or sources can acquire data in a multiplex manner. When using LEDs or multiple single element detectors, they can be energized using Hadamard transform techniques. Through Hadamard transform optical coding techniques the (theoretical) signal-to-noise ratio gains at constant observing time when compared with conventional point-by-point image scanning, can be as high as $1/2N^{1/2}$, where N is the total number of image resolution elements. The principles of Hadamard transformation are explained in the following articles: "Fourier and Hadamard transform methods in Spectroscopy", by A. G. Marshall, et al., *The Journal of Analytical Chemistry* Vol. 47, No. 4, pp 491A–504A, April 1975 and "Hadamard Transform Image Scanning", by J. A. Decker, Jr., *The Journal of Applied Optics,* Vol. 9, No. 6, pp 1392–1395, June. 1970.

With Hadamard transform methods, during operation approximately half of the total number of single wavelength emitting devices are energized for a measurement observation. During the second observation a different set of diodes will be energized. The process continues until N (the number of diodes) observations have been made. The end result is N different observations expressed as N linear equations. The solution of these equations yields the specific intensity value associated with each specific diode. Through the Hadamard approach an improvement of a factor of $\sqrt{N}/2$ in signal-to-noise ratio over the conventional one-diode-at-a-time measurement is achieved because half the diodes are energized during each observation, rather than just one. Thus, in the preferred embodiment the diodes or detectors may be energized via Hadamard transform optical coding techniques to maximize signal-to-noise ratios for a given measurement time.

In view of the foregoing, it is an object of this invention to provide an apparatus and associated methodology for the repeatable procurement of spectral data which can be analyzed for noninvasive measurement of blood analytes. More specifically, the objectives of the current invention are to provide a device:

1. Which enables maximal use of the various wavelength regions that include spectral information on the blood analyte of interest, (e.g. glucose);
2. Which optimizes the path, depending upon the propagation characteristics of the wavelength used;
3. Decreases or compensates for the influence of those substances present in the body that exhibit spectral overlap and have varying concentrations;
4. Which reduces the spectral variability between people and allows for more accurate analyte measurement;
5. Decreases the effects of arterial pulsations;
6. Reduces the affect of body part temperature differences through a thermostated sampling device;
7. Which is rugged and does not require frequent recalibration; and
8. Which uses acousto-optic tunable filters (AOTFs), or other suitably rugged optical instrumentation.

SUMMARY OF THE INVENTION

An improved method of determining noninvasively and in vivo one or more unknown values of a known characteristic, particularly the concentration of an analyte in human tissue. The method includes: (1) irradiating the tissue with infrared energy having at least several wavelengths in a given range of wavelengths so that there is differential absorption of at least some of the wavelengths by the tissue as a function of the wavelengths and the known characteristic, the differential absorption causes intensity variations of the wavelengths incident from the tissue; (2) collecting at least some of the wavelengths whose intensity has been changed by the differential absorption; and (3) calculating the unknown values of the known characteristic. The improvement includes the steps of: (1) providing a first path through the tissue; (2) optimizing the first path for a first sub-region of the range of wavelengths to maximize the differential absorption by at least some of the wavelengths in the first sub-region; (3) providing a second path through the tissue; and (4) optimizing the second path for a second sub-region of the range, to maximize the differential absorption by at least some of the wavelengths in the second sub-region. The range of wavelengths is between 400 nm and 2400 nm.

In the preferred embodiment a third path through the tissue is provided for, which path is optimized for a third sub-region of the range. The first path is optimized for wavelengths between 2000–2400 nm; the second, for wavelengths between 1400–2000 nm; and the third, for wavelengths in the region of 400–1400 nm. The first path has a length of between 0.5–3.0 mm; the second, 4.0–7.0 mm; and the third, approximately 10 mm.

With the foregoing arrangement, the intensities of the wavelengths which traverse the first path can be compensated for by the intensities of the wavelengths which traverse one of the other paths (which are different) to reduce spectral variations which are the result of tissue differences (e.g., melanin and temperature).

At least one of the paths represents a partial transmission path through the tissue. This partial transmission path may pass through the nail of a finger once and, preferably, twice.

The improved method may also include: (1) reducing the arterial pulsations within the tissue; and (2) maximizing the blood content in the tissue.

The apparatus includes: (1) at least one source of infrared energy; (2) at least one detector; (3) a finger sampling device for repeatedly positioning the tissue relative to the source(s) and the detector(s); (4) apparatus, including the source(s) and the detector(s), for generating and measuring the intensities of a first set of wavelengths having transversed the tissue by a first path; and (5) apparatus, including the source(s) and the detector(s), for generating and measuring the intensities of a second set of wavelengths having transversed the tissue by a second path. The apparatus also includes apparatus for dispersing the infrared energy (e.g., filters, gratings, prisms, interferometers and AOTFs).

BRIEF DESCRIPTION OF THE DRAWINGS

FIGS. 9A, 9B and 9C illustrate three alternate sampling configurations for optimizing the pathlength-wavelength relationship;

FIG. 17A is an enlarged view of the tungsten-halogen light source of FIG. 17;

FIG. 31 is a schematic diagram of those instrument embodiments wherein dispersion of the light occurs following irradiation of the finger;

DESCRIPTION OF PREFERRED EMBODIMENTS

Figure 1:
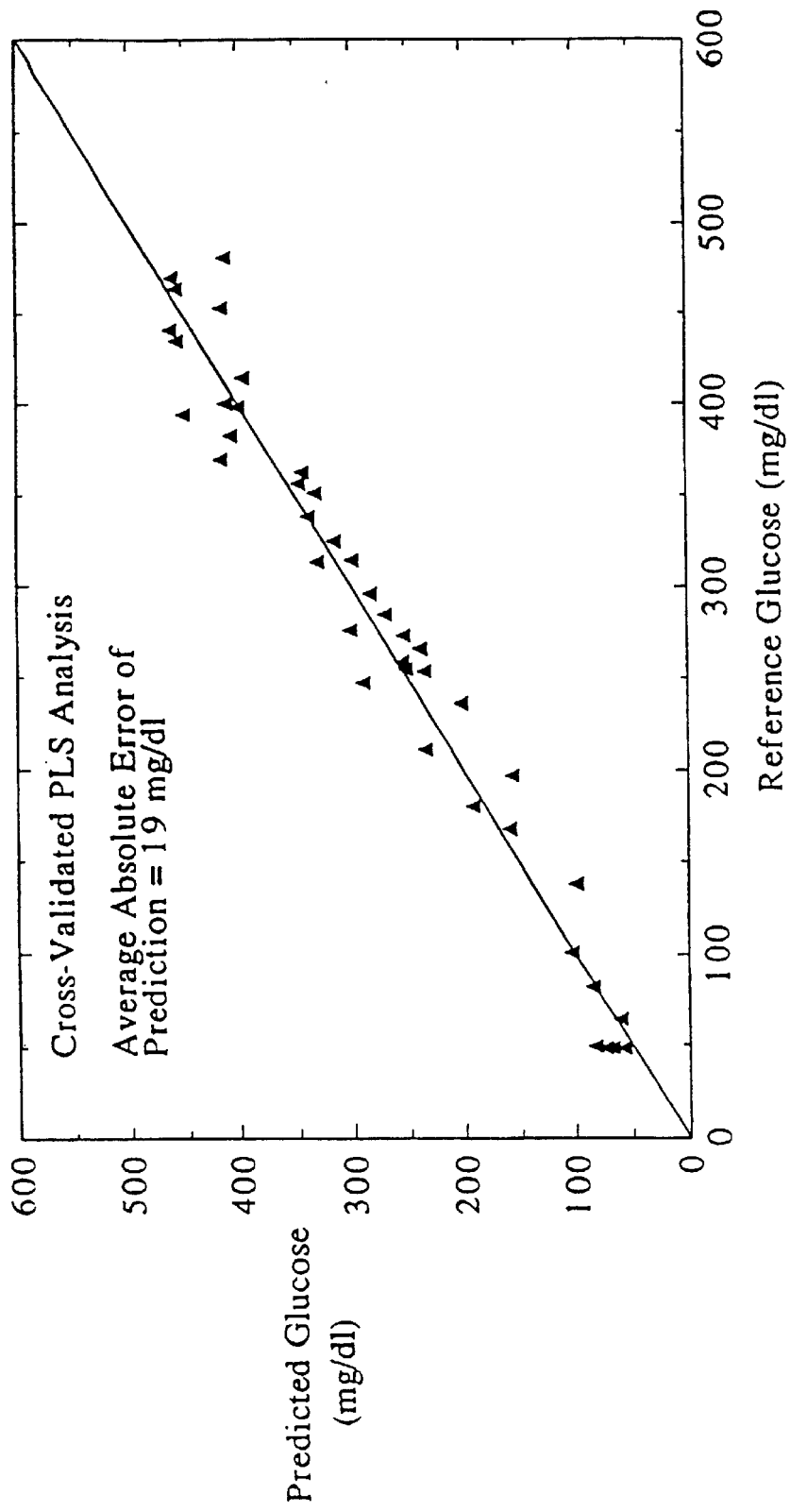
FIG. 1 is a graph illustrating the correlation between Reference Glucose (as determined by conventional invasive procedures) and Predicted Glucose from FTIR spectrometer data.
Figure 2:
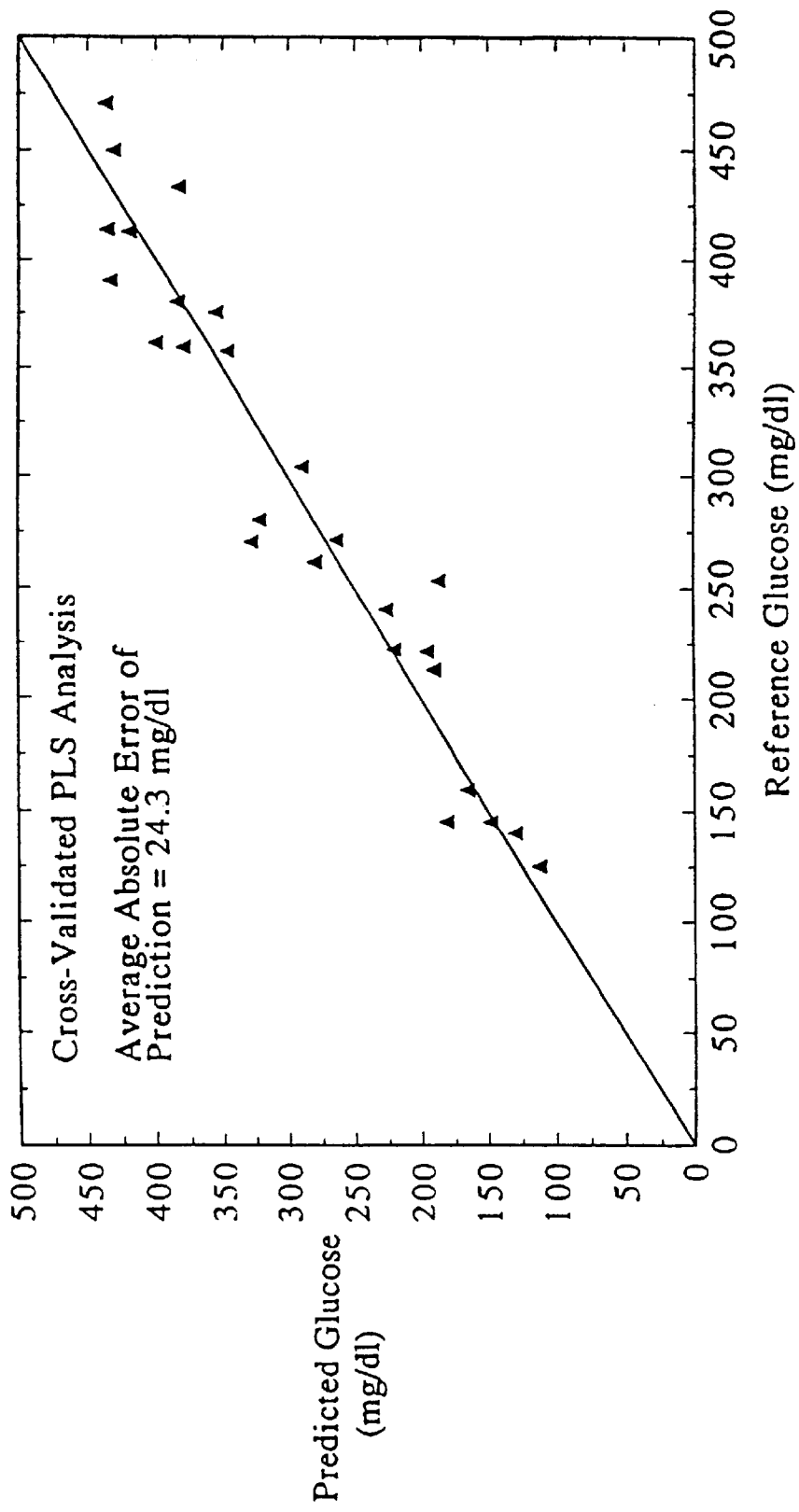
FIG. 2 is a graph illustrating the correlation between Reference Glucose and Predicted Glucose from Grating Spectrometer Data.
Figure 3:
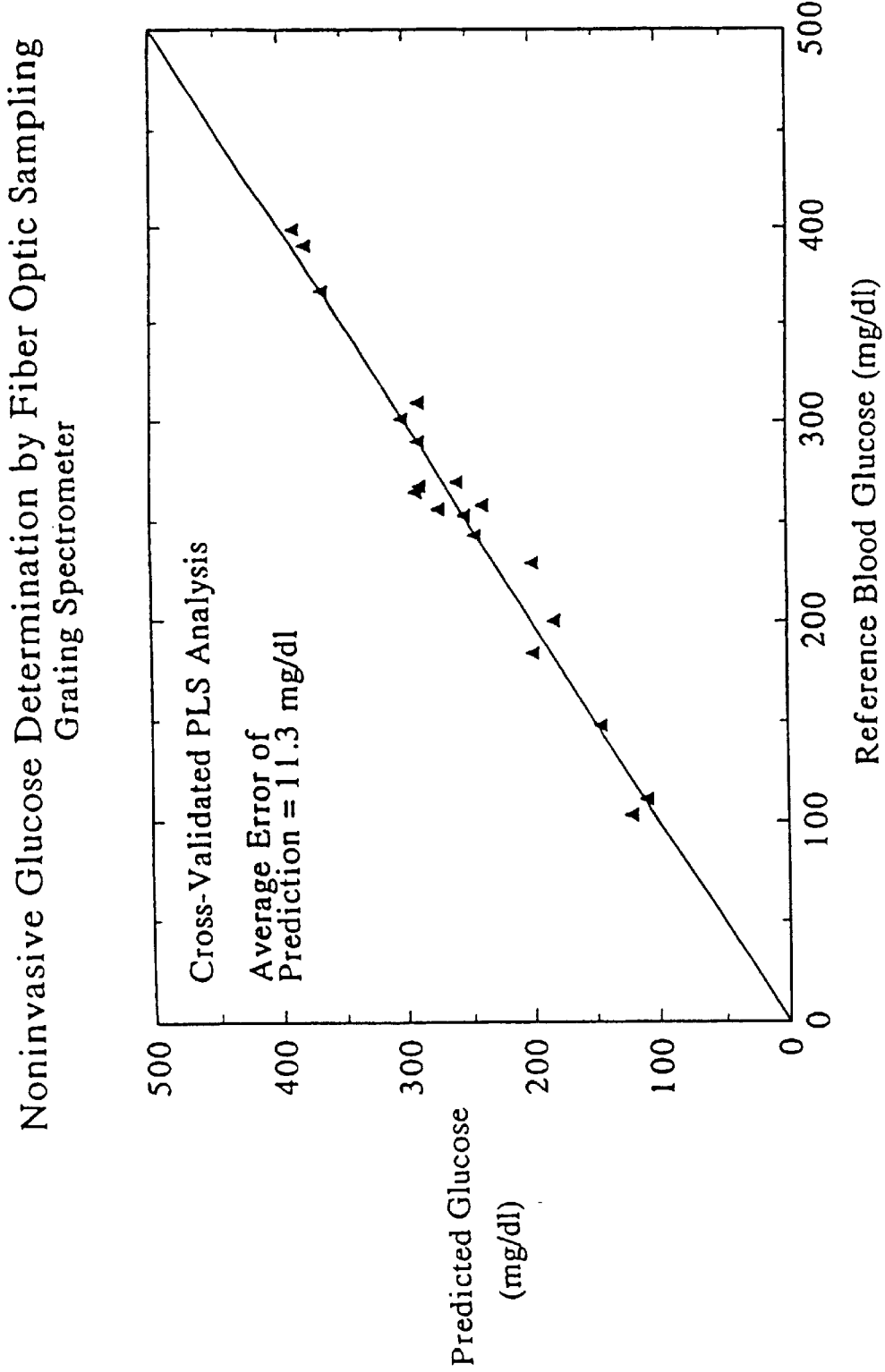
FIG. 3 is a graph illustrating the correlation between Reference Glucose and Predicted Glucose by Fiber Optic Sampling.
Figure 4:
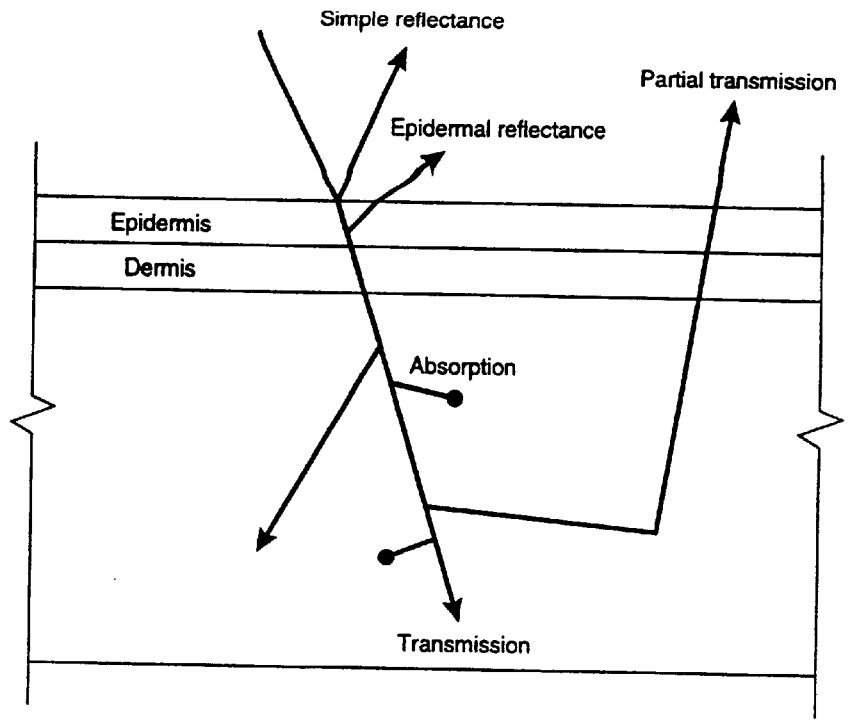
FIG. 4 is a simplified schematic of the propagation characteristics of light within human tissue.
Figure 5:
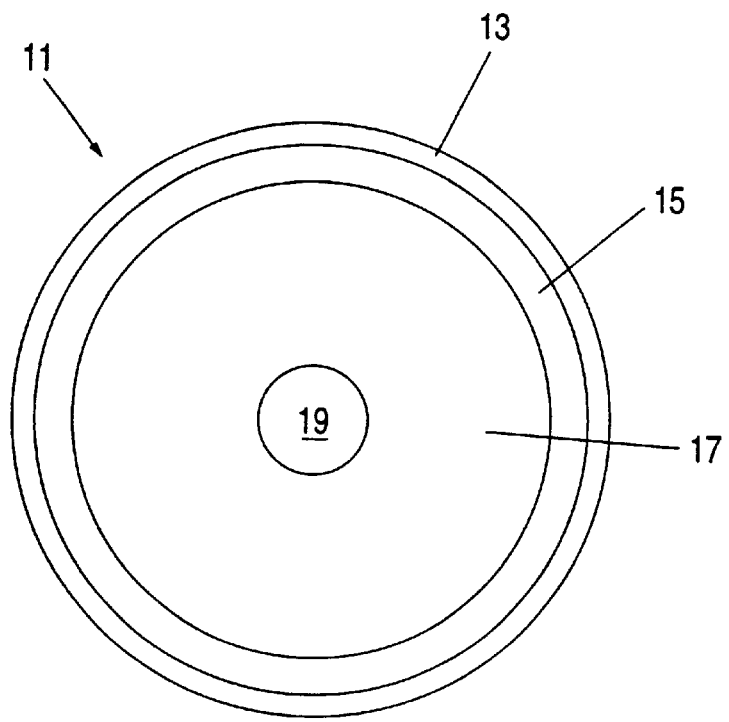
FIG. 5 is a simplified model of a finger.
Figure 6:
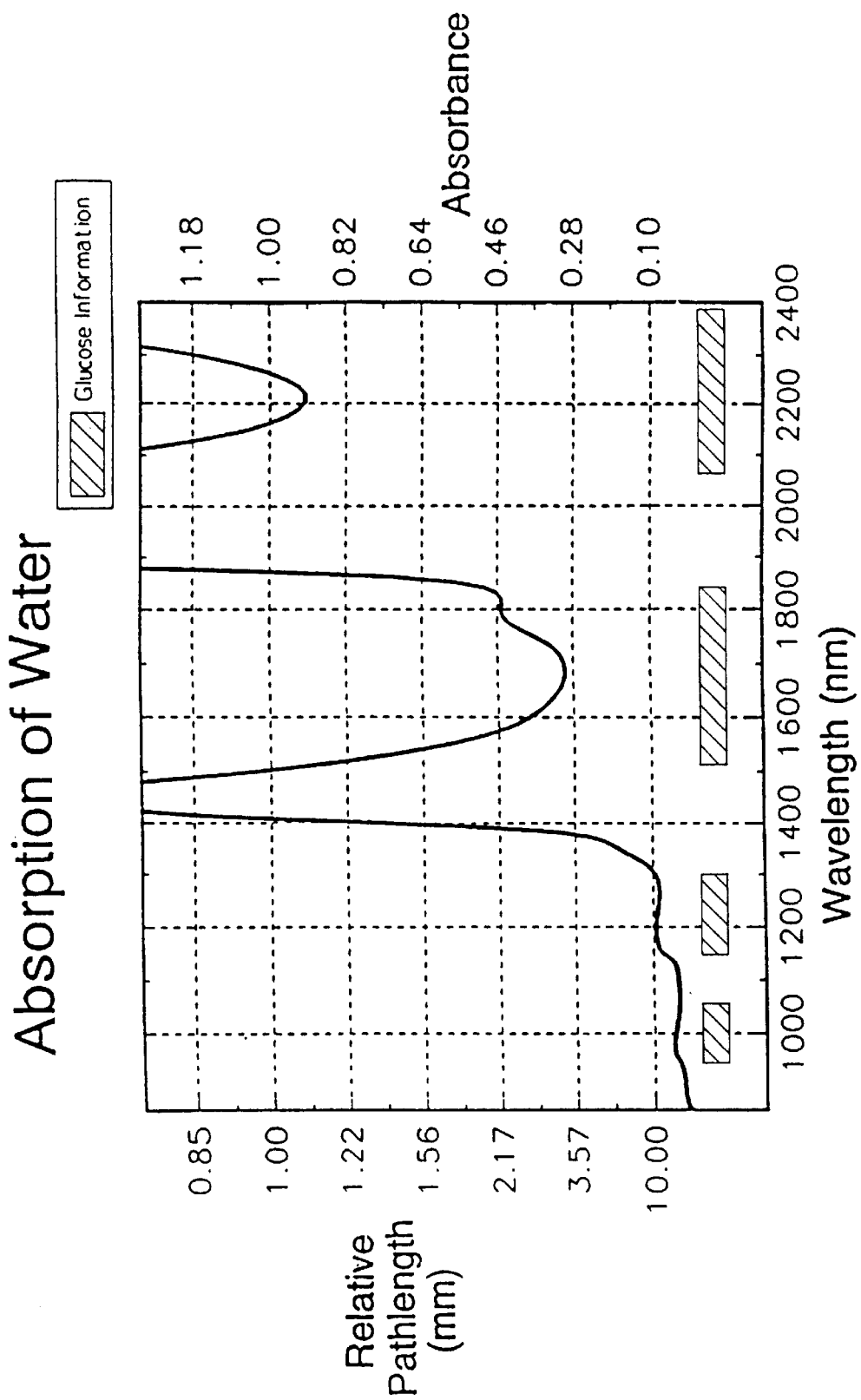
FIG. 6 shows the relationship of both the absorbance of water and the relative pathlength to wavelength used.
Figure 7:
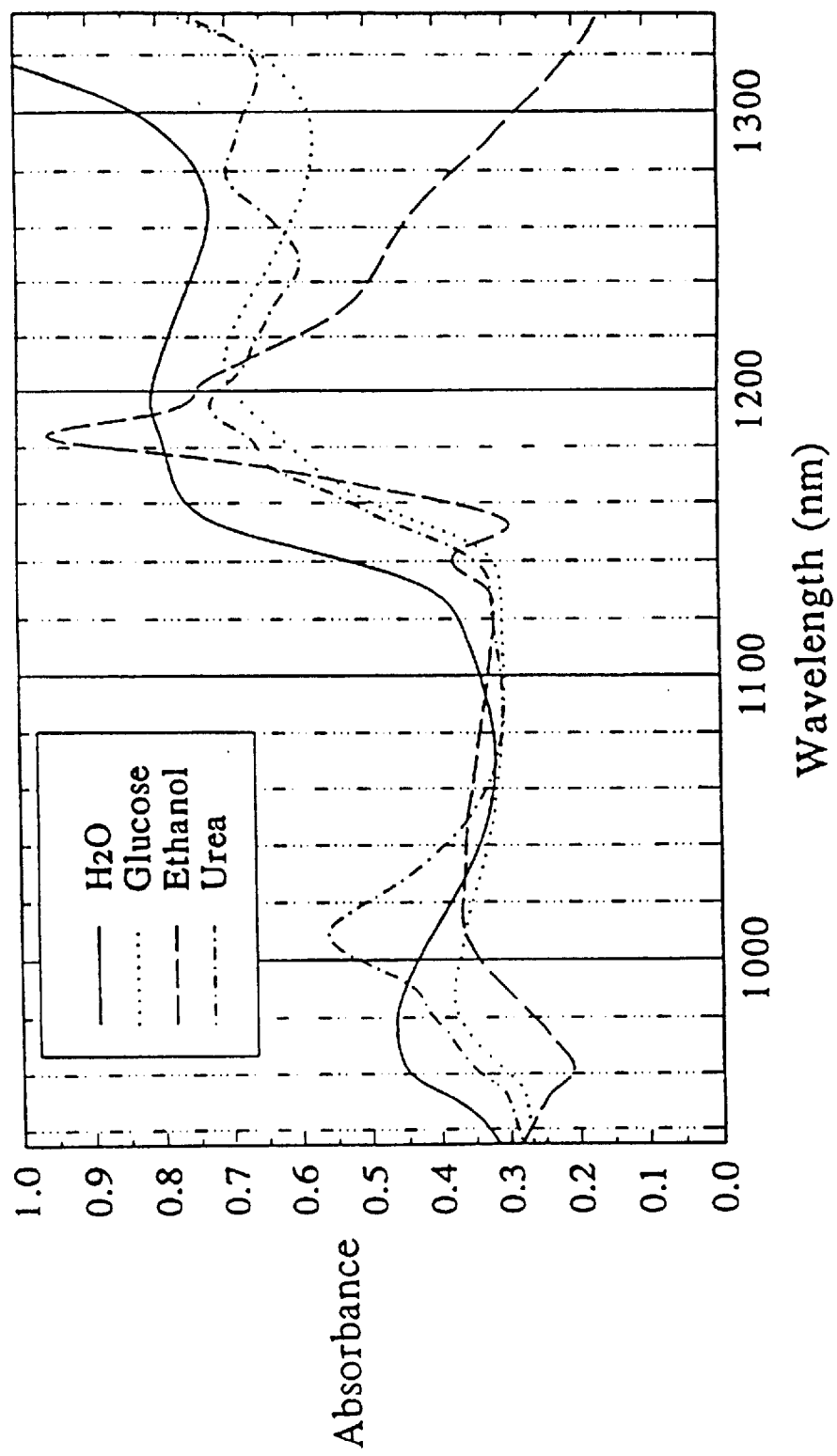
FIG. 7 shows the pure component absorbance spectra for water, glucose, alcohol and urea.

As discussed in relation to in FIG. 6 supra, the relative pathlength varies considerably depending upon the wavelength of light used. FIGS. 9A, 9B and 9C illustrate three alternate sampling configurations which optimize the pathlength relative to the wavelength(s) selected. As those skilled in the art will appreciate, the relative positioning of the source and detector on finger/thumb 11 will influence the internal volume of tissue sampled spectrophotometrically. In FIG. 9A the source 21 and detector 23 are placed relatively close to one another. Thus, the average optical pathlength 22 travelled by the sampled light (via partial transmission) is quite short. Dashed lines (e.g., 24) represent some of the theoretical paths followed by light emitted by a point source placed against finger/thumb 11. If, in the case of glucose, optical information is desired in the 2000 nm region or longer, then the average optical pathlength 22 should be in range of 0.5–3 mm. In addition to the 2000–2400 region, this optical sampling configuration enables measurement of spectral data over the entire wavelength region from 700 to 2400 nm. In FIG. 9A the internal volume sampled will be relatively small, consisting of the epidermis 13 and dermis 15 and the outermost portions of the subcutaneous tissue 17.

Although the sampling configuration in FIG. 9A enables sampling of spectral data from 700 to 2400 nm, the spectral data acquired in the 700–1400 nm region is not acquired under optimal conditions. Given similar signal-to-noise ratios, spectral data in the 700–1400 nm range, obtained by the sampling geometries illustrated in FIGS. 9B and 9C, will contain more analyte information than spectra obtained from the geometry illustrated in FIG. 9A. With similar intensity values at the detector, the information content of the spectra from FIG. 9A is less, due to the fact that a smaller portion of the internal volume of finger/thumb 11 is sampled by the light. In the configuration shown in FIG. 9A, 100% of the light is not forced to transverse the greater distances illustrated by FIGS. 9B and 9C and, thus, does not contain as much information from the deeper subcutaneous tissue.

In FIG. 9B the detector 23 and source 25 are separated by a greater distance and the resulting average partial transmission pathlength 26 is longer. If the average pathlength 26 is assumed to be in the range of 3–7 mm, then the amount of light successfully transversing this distance with wavelengths longer than 2000 nm will be negligible in comparison to those which transverse a 0.5–3 mm pathlength. However, this pathlength represents a reasonable pathlength for light in the region from 1400 to 2000 nm, and also enables measurement of wavelengths below 1400 nm.

FIG. 9C depicts a transmission measurement through finger/thumb 11. The finger thickness of an average individual is, approximately, 1 cm. The influence of the bone in transmission is poorly understood and, thus, the ray tracings go around the bone for simplicity. The resulting optical information received by detector 23 from source 29 will be in the wavelength region from 700 to 1400 nm. The spectral information above 1400 nm will be negligible due to water absorbance at these longer wavelengths.

Figure 10A:
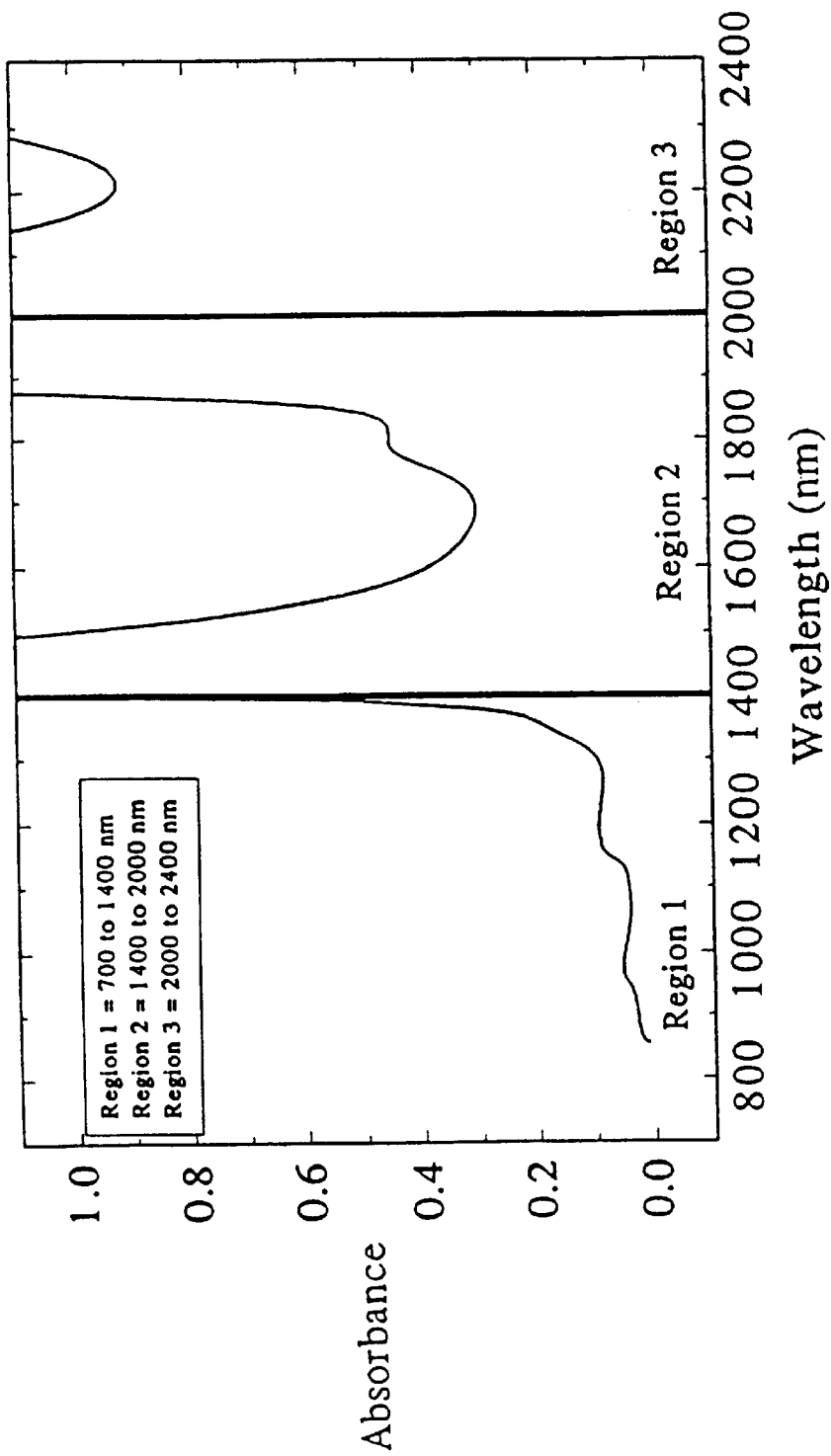
FIGS. 10A, 10B and 10C are plots illustrating the spectral regions that can be recorded by the three different source-detector configurations of FIGS. 9A, 9B and 9C.
Figure 10B:
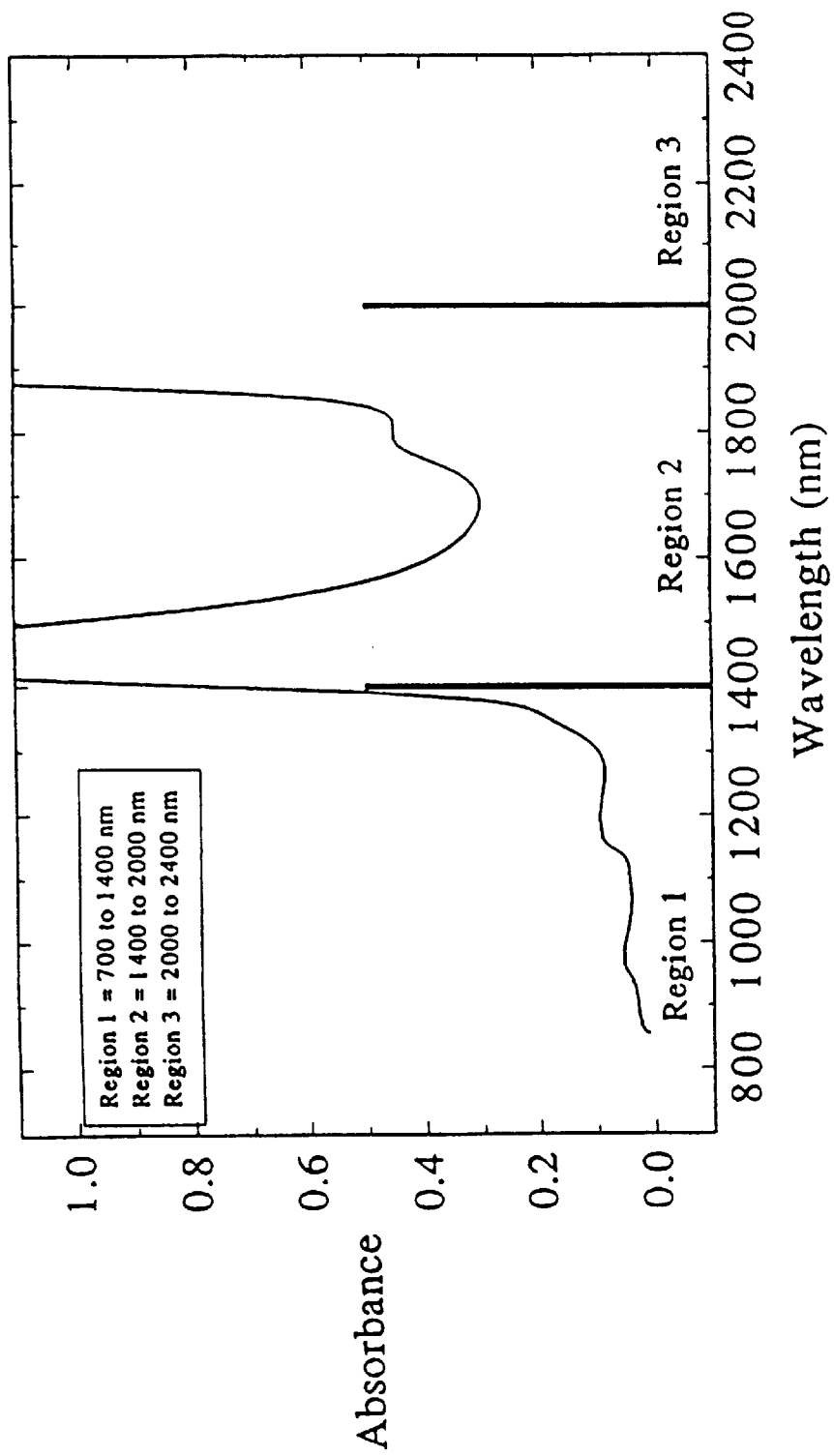
Figure 10C:
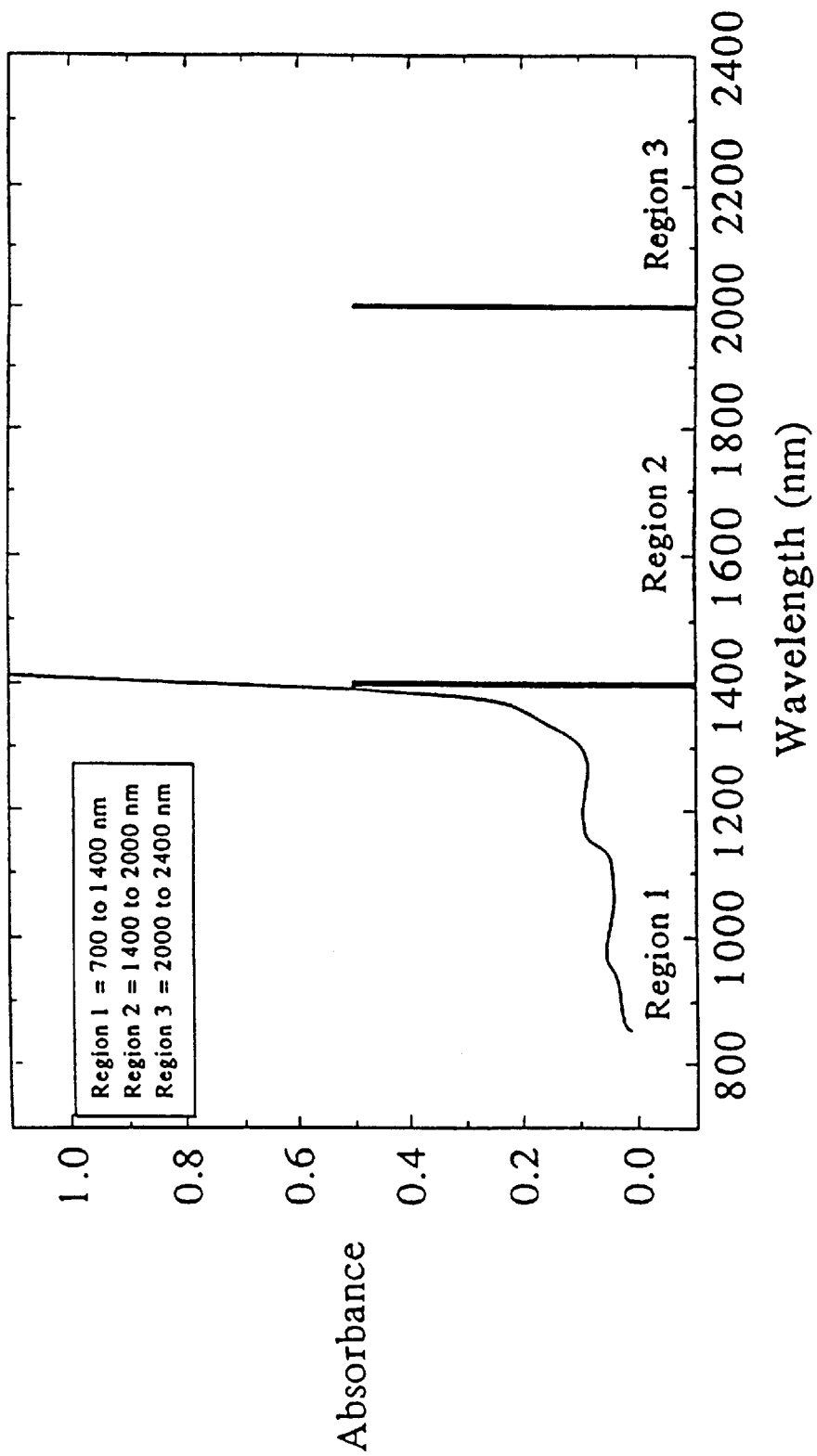
Figure 11:
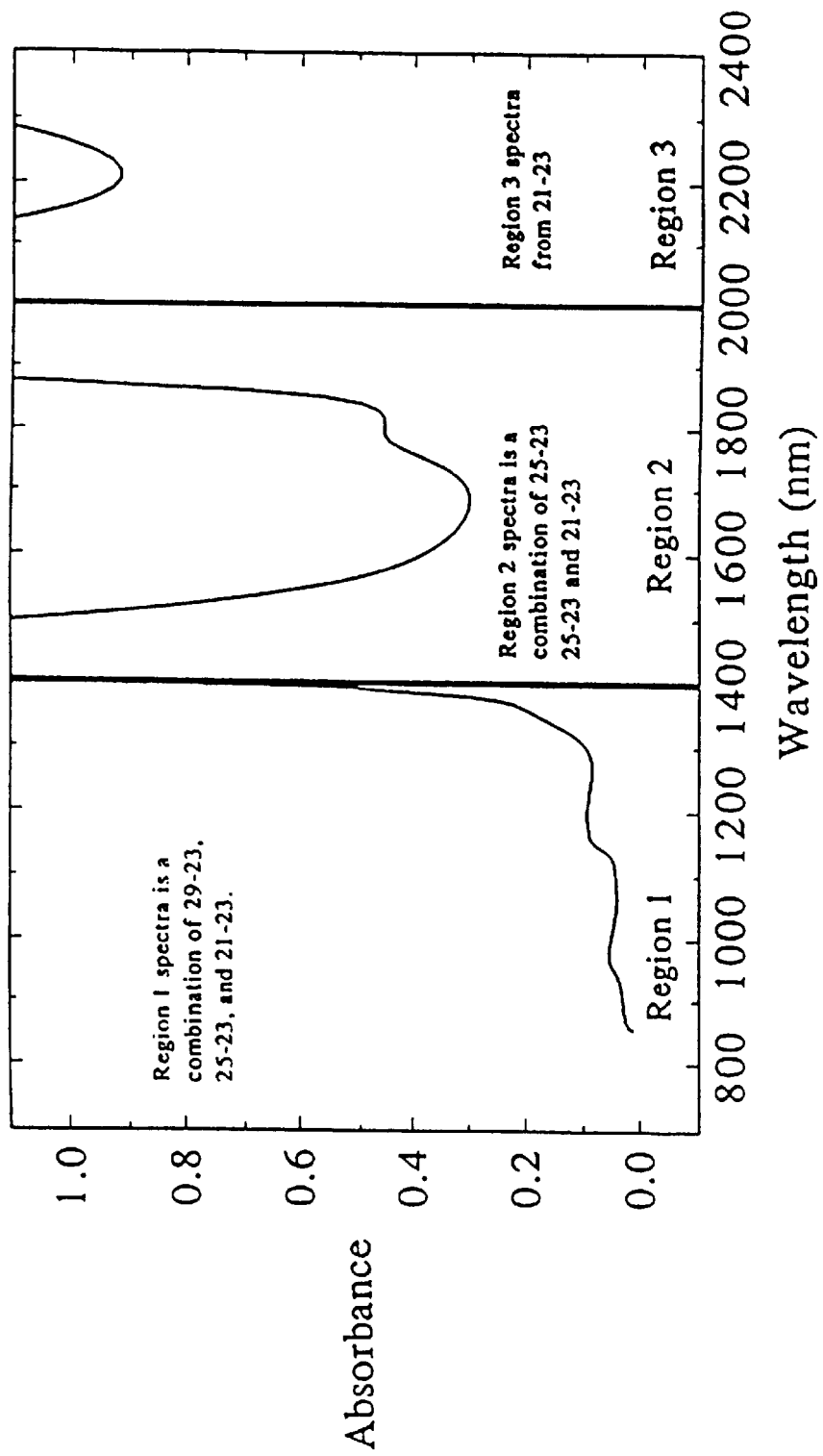
FIG. 11 is a plot of the spectra composed from the different source-detector configurations illustrated in FIGS. 9A, 9B and 9C.

The geometric configurations shown in FIGS. 9A, 9B and 9C enable procurement of optimal spectral data for glucose in each wavelength region (i.e. 700 to 1400, 1400 to 2000, and 2000 to 2400) in the best possible manner. For clarification the spectral range of interest is divided into 3 regions:

Region 1 from 700–1400 nm; Region 2 from 1400–2000 nm; and Region 3 from 2000–2400 nm. FIGS. 10A, 10B and 10C are plots showing the spectral regions that can be recorded by each of the three source-detector configurations. FIG. 10A is the spectral data which can be recorded using the source-detector configuration shown in FIG. 9A. As previously described, the configuration shown in FIG. 9A can sample all three regions as shown in FIG 10A. FIG. 10B depicts the spectral data obtained when using the optical configuration illustrated in FIG. 9B, which spectral data is in Regions 1 and 2, but not in Region 3. FIG. 10C shows the spectral data generated by using the optical configuration shown in FIG. 9C. In this case, useful spectral information is available only in Region 1. FIG. 11 is a plot of the resulting spectra from the source detector arrangements illustrated in FIGS. 9A, 9B and 9C. The resulting spectra contains the maximal amount of analyte information due to optimization of sampling path in each of the three wavelength regions.

The spectrum of FIG. 11 can be further improved by removal of the spectral variations introduced by melanin and other patient variations. Specifically, spectra which is indicative of the internal tissue glucose (independent of the individual, and without such factors as degree of pigmentation, age, skin thickness, and differences in peripheral-skin temperature) is uniquely useful when doing quantitative measurements. As the intrinsic volumes sampled by the various source-detector geometries illustrated in FIGS. 9A, 9B and 9C are different, these differences can be used to remove many undesired influences (e.g. melanin). Returning to FIGS. 9A, 9B and 9C, it can be seen that all source-detector combinations require the light to transverse epidermis 13 and dermis 15 twice. This is true whether the measurement is made through skin only or the fingernail. In the 700 nm to 1100 nm region (i.e., Region 1) the spectral information obtained by using source 21 with detector 23 will correspond to skin information twice, plus a small amount of information on the underlying tissue. In comparison, the spectral information obtained by using source 29 with detector 23 will contain skin information twice, plus a large amount of information on the underlying tissue. The differences in the volumes sampled by the different sampling geometries can be used to cancel out or minimize skin specific differences. As melanin resides solely in the outer layers of skin, the spectra obtained via the two sampling configurations can be processed to yield spectra which minimizes spectral variations which are the result of pigmentation differences. Specifically, Beer's Law and the relationship of mean optical pathlength with the length of the physical path can be utilized by a ratio and subtraction process to yield the desired spectra. The coefficient values to be used in association with Beer's Law are determined by experimental investigation and are instrument/configuration dependent.

Differences in peripheral skin temperature can also be removed by using differences in the volumes sampled by the various sampling configurations. The skin temperature of the hand varies greatly from person to person and is also dependent upon the environment. Despite peripheral skin temperature variations, body core temperature remains quite constant. The internal tissue of the hand will be maintained at relatively constant temperature due to constant exposure to core temperature blood. Thus, the temperature differences between people's hands exist in the dermis and epidermis while the underlying tissue remains well thermostated. As temperature differences are present in the outermost layers of the skin, the difference in the volumes sampled can again be used to help minimize spectral variation not associated with analyte concentration. Thus, skin temperature differences can be compensated for in a manner similar to melanin.

The sampling configurations illustrated in FIGS. 9A, 9B and 9C satisfy objectives 1 and 2 of the invention, but do not reduce all possible spectral variations between patients. Specifically, the spectral information obtained by transmission through the finger (i.e. use of source 29 and detector 23) will be sensitive to tissue thickness differences. However, such differences in tissue thickness can be minimized by performing the sampling by partial transmission sampling and by sampling from the same side of the tissue, wherein the tissue can be a finger, thumb, or other body part.

Figure 12:
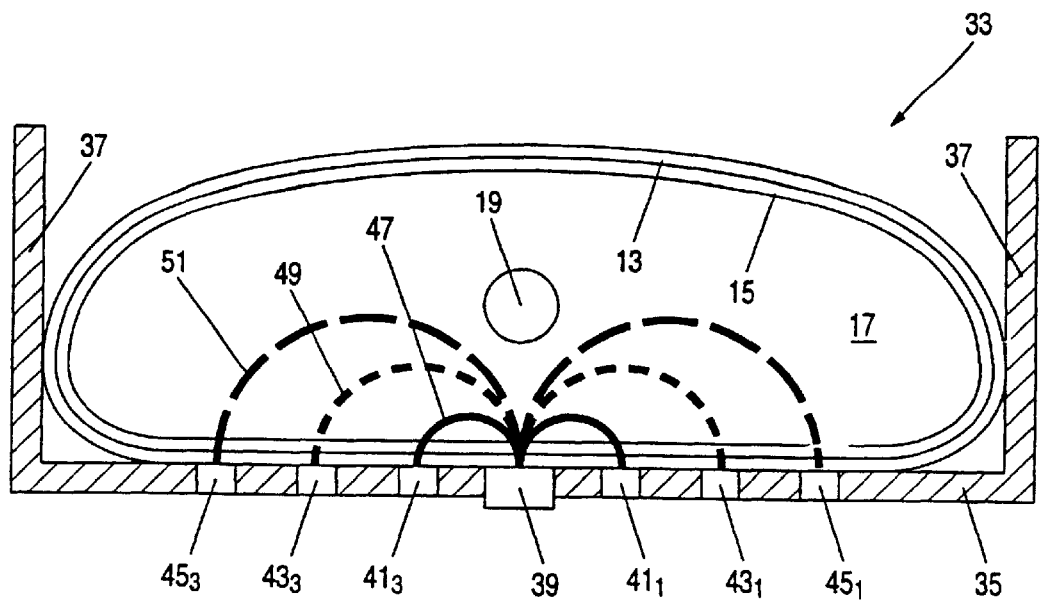
FIG. 12 is a cross-sectional view of a finger holding device of the present invention.
Figure 13:
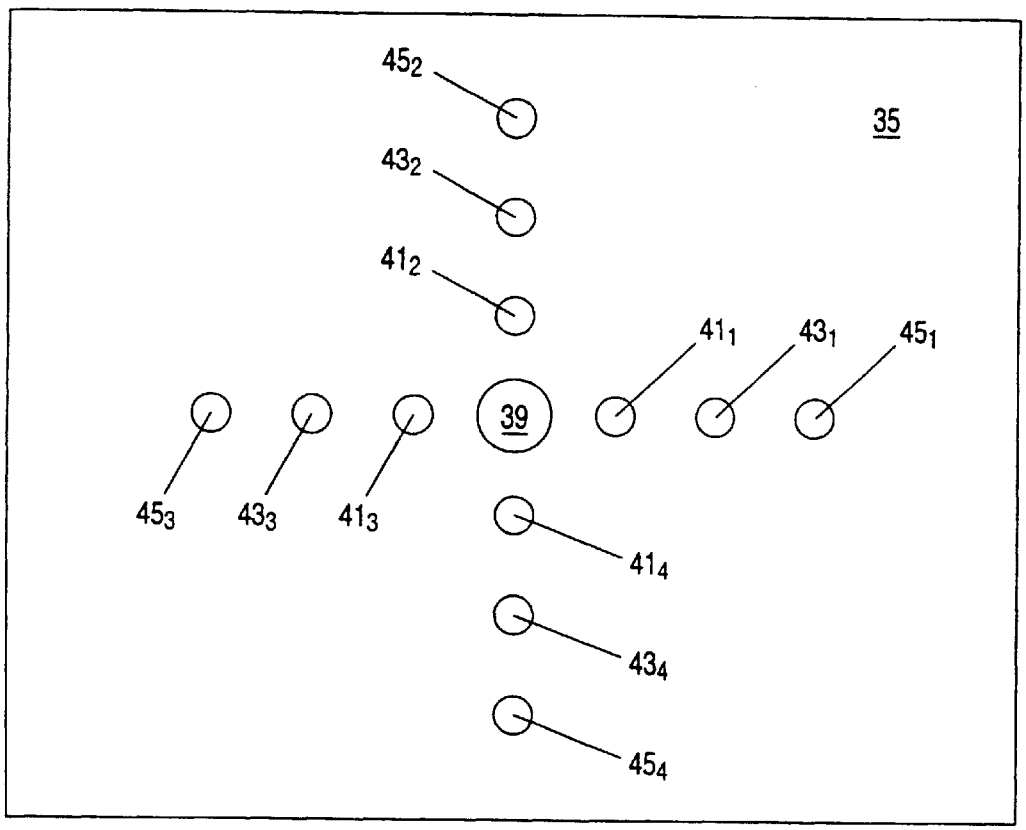
FIG. 13 is a bottom view of the device illustrated in FIG. 12.

With reference to FIGS. 12 and 13, finger/thumb holder 33 includes a bottom plate 35 and a pair of guide rails 37. Positioned substantially in the center of plate 35 is a detector 39 and a plurality of sources $41_{1-4}$, $43_{1-4}$ and $45_{1-4}$. The average light path from sources $41_{1-4}$ to detector 39 is approximated by path 47; from sources $43_{1-4}$ to detector 39, by path 49; and from sources $45_{1-4}$ to detector 39, by path 51. As was illustrated in FIGS. 9A, 9B and 9C, the optical sampling of the body part must maximize and compensate for the optical propagation characteristics of different wavelengths. In FIG. 12 light path 47 represents an optical pathlength of 0.5–3 mm, which is the same pathlength as illustrated in FIG. 9A. Light path 49 is similar to that shown in FIG. 9B, and light path 51 is similar to that shown in FIG. 9C. In either sampling geometry the relationship between the source and detector determines the length of the optical path and the depth of the internal volume sampled. For each distance a plurality of light sources is used to increase the intensity at detector 39, and to reduce the total measurement time.

Figure 14:
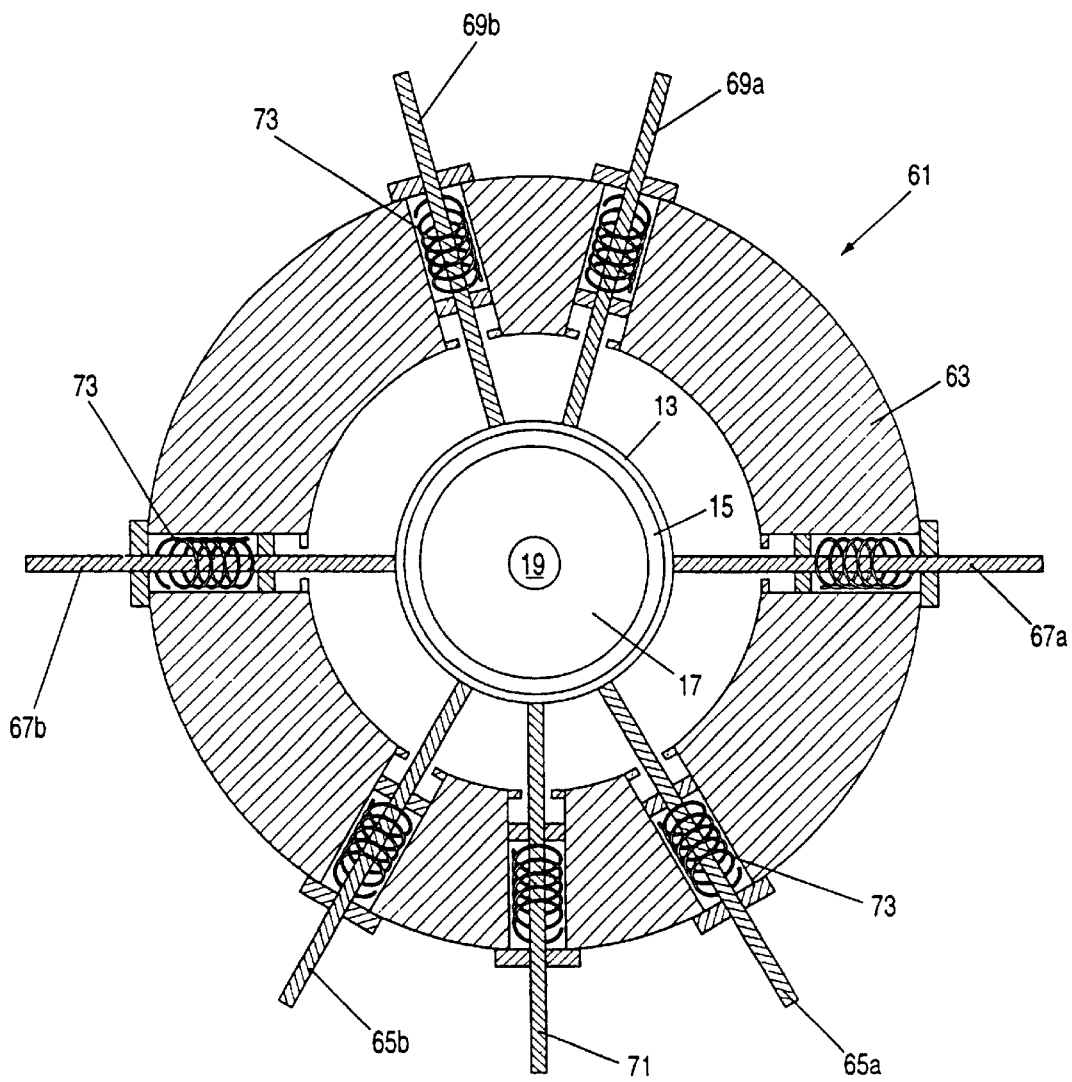
FIG. 14 is a cross-sectional view of an alternate finger sampling device of the present invention.
Figure 15:
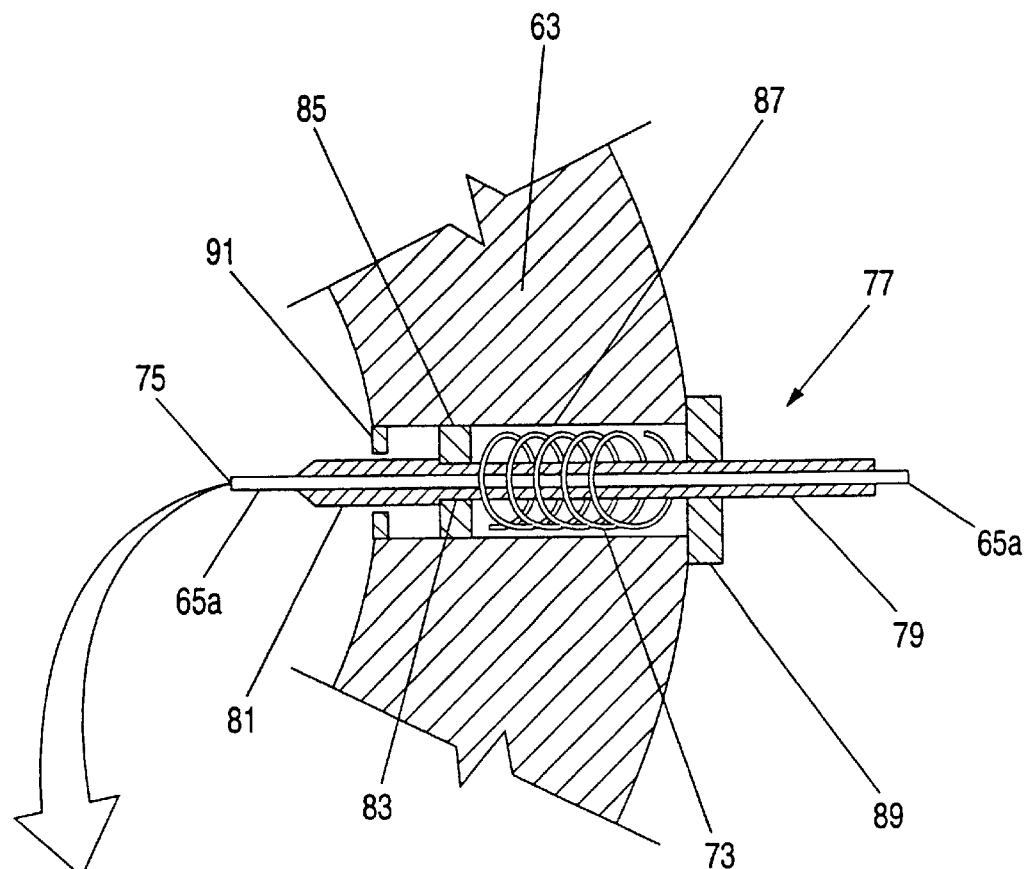
FIG. 15 is an enlarged, partial sectional view of the apparatus illustrated in FIG. 14.
Figure 15A:
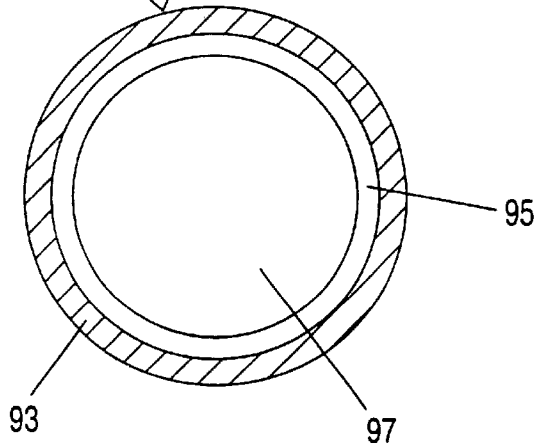
FIG. 15A is an enlarged end view of the fiber optic probe of FIGS. 14 and 15.

A variety of embodiments can be utilized to enable sampling of the finger/thumb in an optimal manner. FIG. 14 illustrates a device 61 using fiber optics to introduce light into the finger/thumb 11 at three different sampling geometries. In the device shown, housing or ring 63 supports six different fiber optic probes 65a and 65b, 67a and 67b, and 69a and 69b which introduce the light into the tissue in three different source-detector configurations. Detector probe 71, also supported by housing 63 receives the light which has transversed the tissue. Fiber probes 65a–69b and detector probe 71 are all spring loaded, via springs 73, to enable repeatable interactions between the tip of each fiber, as indicated at 75 in FIG. 15, and finger/thumb 11. Each fiber probe is independently spring loaded to enable the sampling device to compensate for the elliptical shape of the finger. As also indicated in FIG. 15, representative probe 65 a is held by a hollow fiber holding device 77 which includes a hollow stem 79 and a shoulder 81. Stem 79 is held in bore 83 by collar 85 which, in turn, is slidably received in bore 87 in housing 63. Spring 73 is captured between collar 85 and cap 89 which is threaded into housing 63 (by threads not shown) or otherwise suitably secured. Bore 87 has an internal shoulder 91 to prevent collar 85 from falling out. Probes 65b–69b and detector 71 have the same structure as probe 65a. FIG. 15A illustrates, on an enlarged scale, the end of a typical probe (e.g. 65a), including metal sheath 93, surrounding external cladding 95, which in turn surrounds optical fiber 97.

The angular relationship between fiber optic probes 65a and 65b, and detector fiber 71 is, approximately, 30 degrees. This geometrical configuration allows, as discussed above, sampling of the spectral region from 700 to 2400 nm. Probes 67a and 67b simultaneously introduce light into finger/ thumb 11 at 90 degrees relative to detector fiber 71. The average optical pathlength will be approximately 3 to 7 mm. The configuration composed of probes 67a and 67b, and fiber 71 will enable sampling of the spectral region from 700 to 2000 nm. The remaining two probes, 69a and 69b, introduce light into finger/thumb 11 on the opposite side of the finger, at approximately 165 degrees relative to fiber 71. Light detected by detector fiber 71 from these 2 probes has propagated through the majority of finger/thumb 11. For glucose, the spectral region measured by this configuration will be from 700 to 1400 nm.

In operation, only one source pair-detector configuration (e.g. 65a/65b–71) is coupling light into finger/thumb 11 at any one time. The operation of the sources is performed in a manner to determine the optical path transversed by the light. If all sources are active at a given point in time then it would be impossible to determine from which point a given photon of light originated. The introduction of light into the finger from two geometrically similar locations (e.g. probes 65a and 65b) increases the total light entering finger/thumb 11, which increases the total amount out of finger/thumb 11 and onto the detector fiber 71. Increasing the intensity at the detector, provided the operation remains linear, is desirable as it reduces total measurement time.

Figure 16:
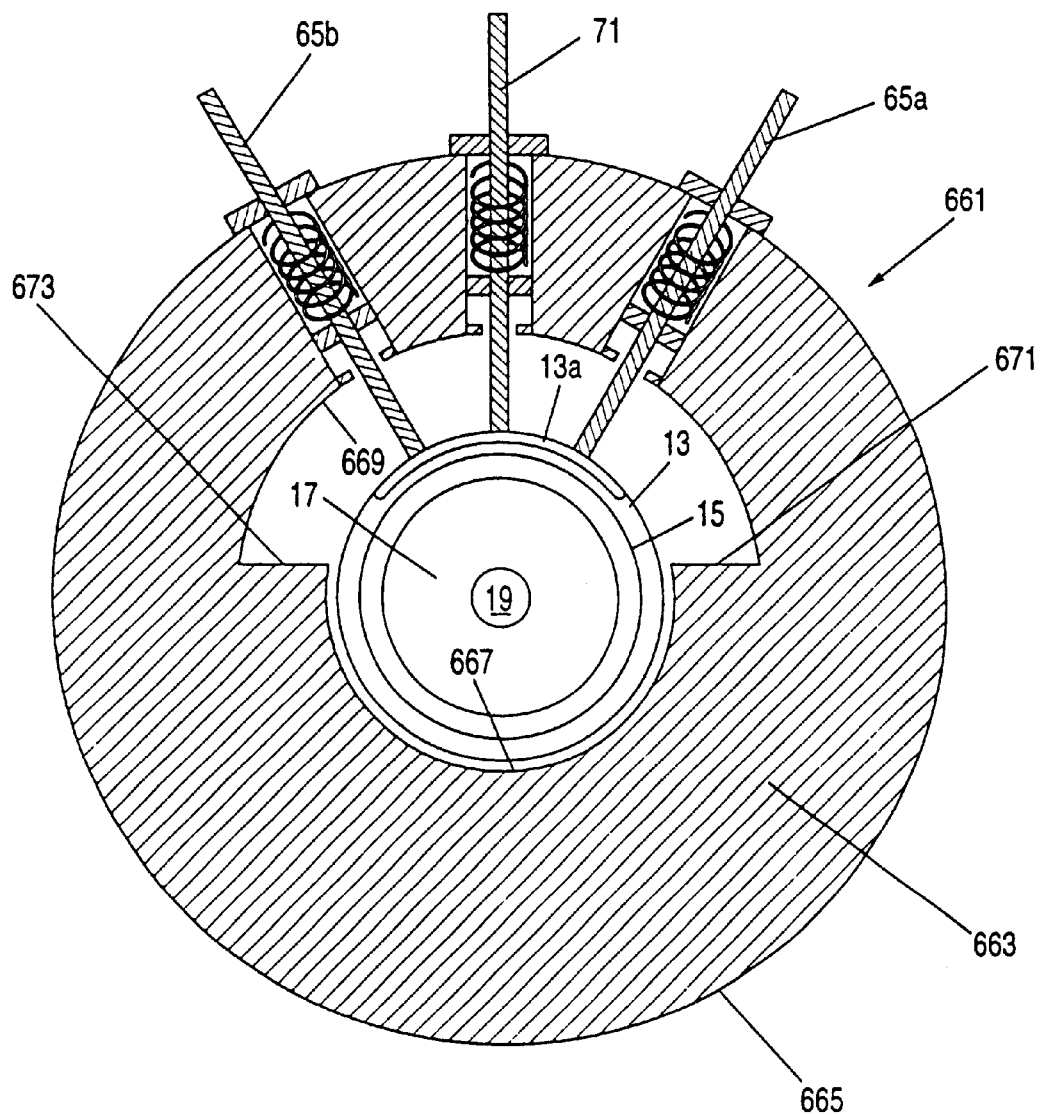
FIG. 16 is a cross-sectional view of a modified version of the finger sampling device illustrated in FIGS. 14–15A.

A modified version of finger sampling device 61 is illustrated in FIG. 16. Device 661 includes a housing or ring 663 having an outer cylindrical surface 665 and two semi-cylindrical surfaces 667 and 669, interconnected by plainer surfaces 671 and 673. As illustrated, the diameter of surface 667 provides a support for finger/thumb 11. Positioned between surfaces 665 and 669 are two fiber optic probes 65a and 65b and a detector 71. Probes 65a and 65b (which are angularly positioned relative to detector 71 by, approximately, 30°) contact fingernail 13a. As previously explained, fingernail 13a is basically optically inert in the region from 700 mm to 2400 mm. Though only two probes are illustrated, additional ones could be provided. FIG. 16 illustrates a sampling device where all optical sampling is performed through the fingernail. The device could be modified to include small tungsten-halogen sources or other configurations. The end result is a sampling device which makes optimal use of this "window" into the body.

Figure 17:
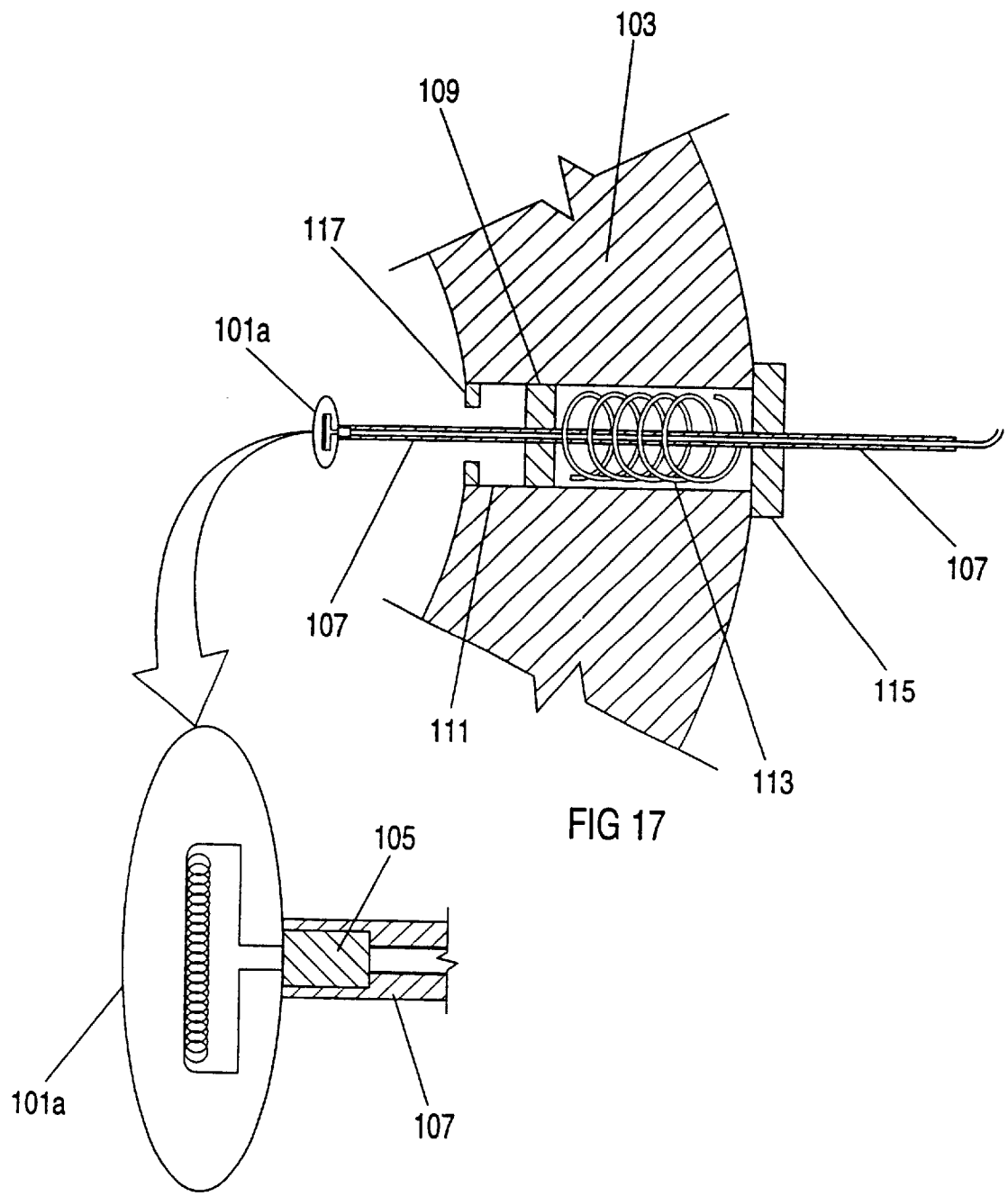
FIG. 17 is an enlarged, partial sectional view of an additional finger sampling device.

FIG. 17 illustrates a sampling device like that of FIGS. 14 and 15, except modified for use of small tungsten-halogen light sources such as manufactured by Welsh Alan. Six light sources, such as source 101a, are arranged on circular housing 103 (which has the same configuration as housing 63) in the same pattern as probes 65a–69b are arranged relative to detector 71. Light source 101a is secured in socket 105 provided on the end of hollow electrical support stem 107. Stem 107 includes a circular collar 109 fixed thereto, which is slidably received in bore 111 provided in housing 103. Spring 113 is captured between collar 109 and end cap 115 (suitably secured to housing 103 ), to bias source 101a into engagement with finger/thumb 11. Lip 117 prevents collar 109 from being pushed out of bore 111. As described previously, this geometry enables spectral measurement over different regions. In operation, the light sources closest the detector will be turned on and spectral data acquired in the 700 to 2400 nm region. Next, the sources at 90 degrees to the detector will be energized and spectral data from 700 to 2000 nm will be recorded. Finally, the sources opposite the detector will be turned on and spectral data from 700 to 1400 nm recorded.

Due to the fact that not all wavelengths need to be recorded and the fact that relatively small number (e.g. 20) will produce good measurement results, a discrete set of light emitting diodes (LEDs) can be utilized instead of broadband sources such as 101a of FIGS. 17 and 17A.

Currently, LEDs are commercially manufactured in the wavelength region from 400 to approximately 1550. However, in the future, diodes will likely become commercially available over the entire spectral region from 400 to 2400 nm. As LEDs emit wavelengths with a narrow bandwidth (i.e., typically less than 10 nm) further dispersion of the spectra is not necessary. As further dispersion is not necessary a simple inexpensive detector or multiple detectors can be used to record the various wavelength intensities.

Figure 18:
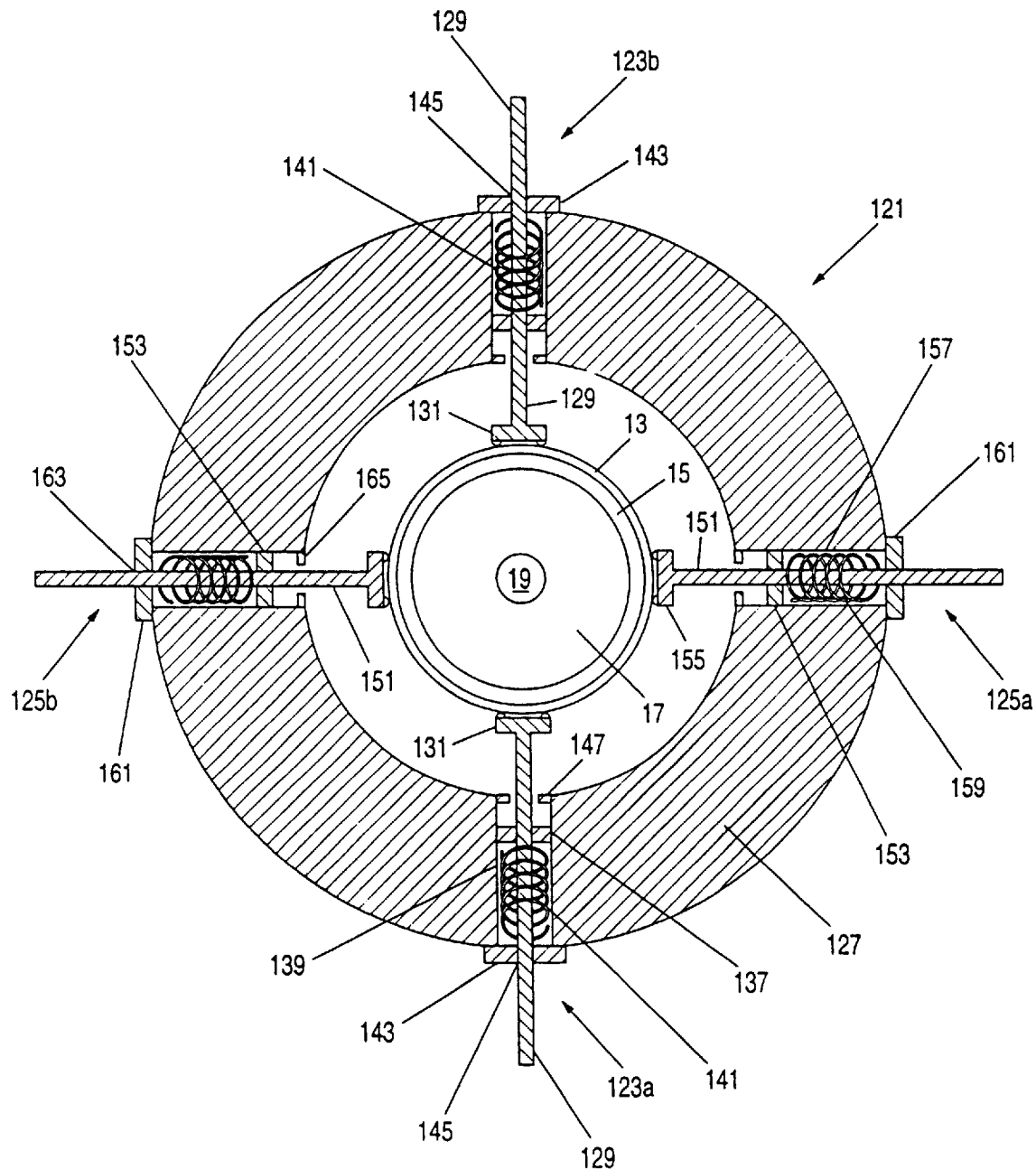
FIG. 18 is a cross sectional view of yet another finger sampling device.
Figure 19:
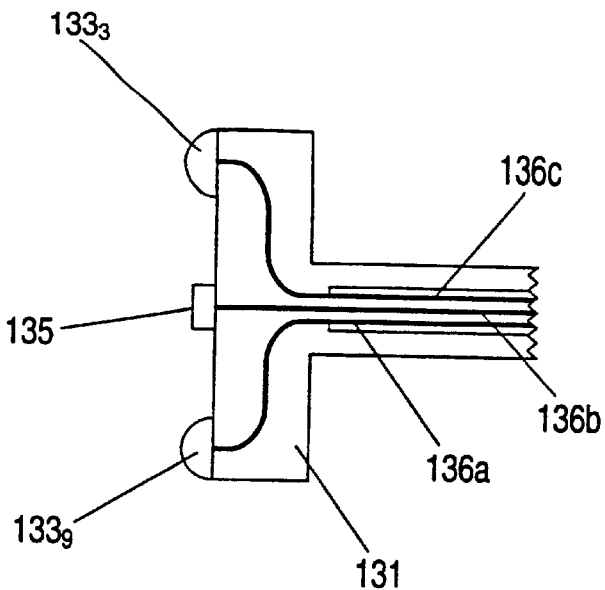
FIG. 19 is an enlarged partially schematic and partially sectional view of one of the LED probes of FIG. 18.
Figure 20:
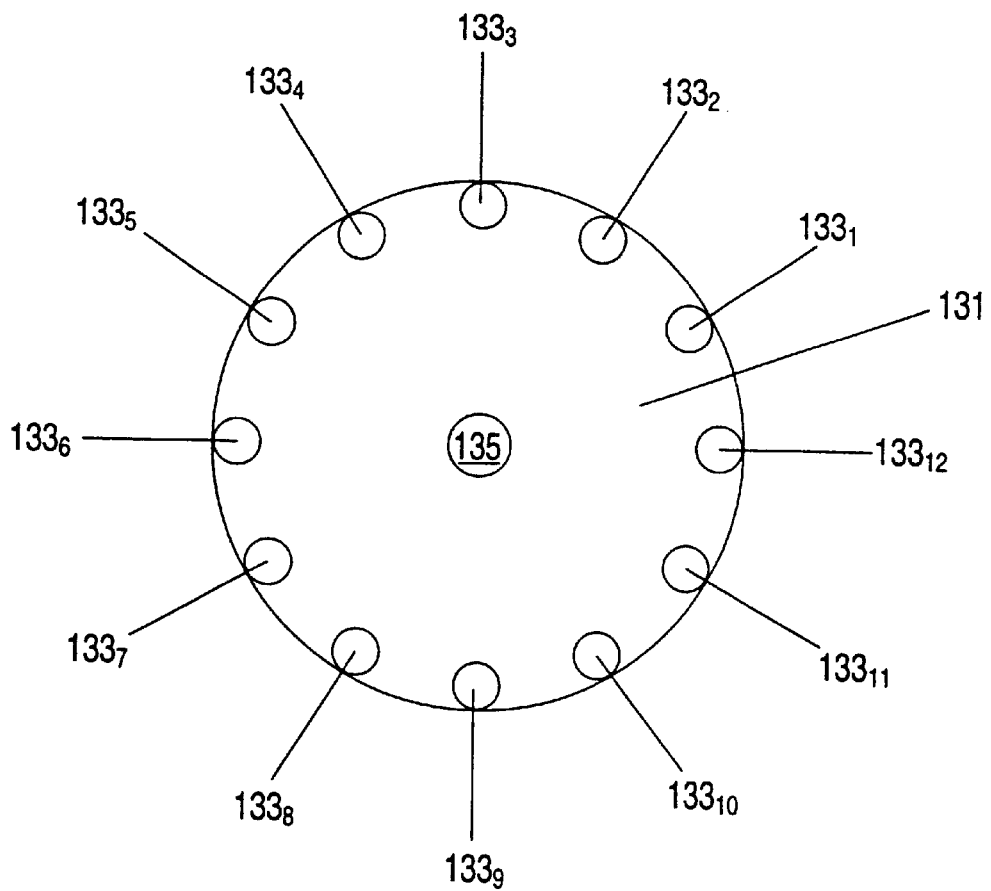
FIG. 20 is an enlarged end view of the LED probe of FIG. 19.

As illustrated in FIGS. 18–21, finger sampling device 121 includes a first set of probes 123a, 123b, and a second set of probes 125a, 125b, mounted at 9° intervals around housing 127. Probes 123a and 123b each include a hollow stem portion 129 (FIG. 19) of circular cross-section and a disc shaped head 131 (FIG. 20). Secured to head 131 near its perimeter (by conventional means not illustrated) are a plurality of LEDs $133_{1-12}$. Secured to the center (also by conventional means not shown) is a detector 135. Detector 135 and LEDs 133 are connected to suitable electrical connectors such as 136a, 136b and 136c. Stem portion 129 also includes a circular collar 137 which is slidably received in bore 139 of housing 127. Probe 123 is biased into engagement with finger/thumb 11 by spring 141 which, in turn, is captured between collar 137 and cap 143 (secured by suitable conventional means, not shown, to housing 127). Cap 143 has a circular opening 145 dimensioned to slidably receive stem 129. Finally, each bore 139 has a shoulder 147 at its inner end to retain collar 137.

Probes 125a, 125b are substantially identical to probes 123, except that they do not include any detectors. Thus, each probe 125 includes a hollow stem portion 151, collar 153 and disc shaped head 155. Collar 153 is slidably received in bore 157 and biased by spring 159, which is captured between collar 153 and cap 161. Cap 161 has a circular opening 163 for slidably receiving stem 151. Bore 157 includes internal shoulder 165.

Figure 21A:
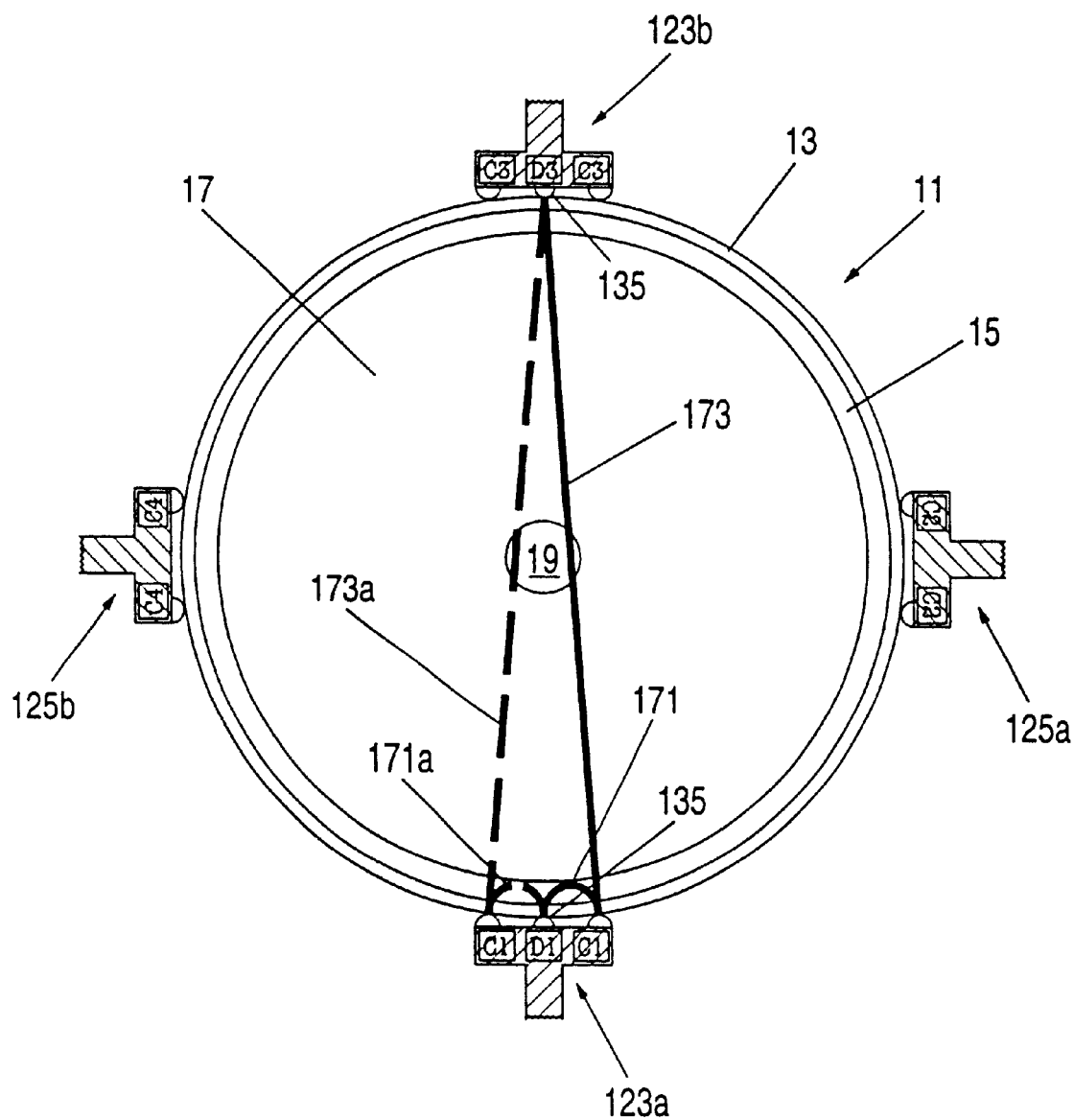
FIGS. 21A, 21B and 21C illustrate various theoretical light paths through the finger with the probes of FIG. 18.

As with those on probes 123, each LED on probes 125 represents a narrow bandwidth source predetermined to obtain important spectral information enabling measurement of the concentration of the analyte (e.g., glucose). Considering only the region from 400 to 1550 nm, the region over which LEDs currently operate, the spectral information (similar to that illustrated in FIG. 11) is obtained by three separate operations using the specific regions of 400 to 1100 nm, 1100 to 1400 nm, and 1400 to 1550 nm. The procurement of spectra in the 400 to 1100 nm region requires the measurement of both short pathlength and long pathlength spectral data, which can be measured at the same time, as illustrated in FIG. 21A. The LEDs $133_{1-12}$ on probe 123a are energized in a manner such that the intensity associated with each LED can be determined. Specifically, the LEDs are energized in accordance with Hadamard transform optical coding techniques. This is done because if every LED was turned on at the same time it would be impossible to differentiate between specific wavelengths. For each LED on probe 123a, the light propagating through the tissue is measured by both detectors 135 simultaneously (detector 135 on probe 123a and detector 135 on probe 123b). Thus, detector 135/123a will measure those photons having transversed a short partial transmission path 171, while detector 135/123b will measure those photons having transversed the entire finger. Solid line 173 illustrates the average path that the light will travel. Dashed lines 171a and 173a represent the average short and long paths between a second LED on probe 123a and detectors 135. The combination of information from these two detectors can be used to remove for skin specific components and result in spectral information ready for analysis, for the reasons discussed above in reference to FIGS. 9A–11. The LEDs on probe 123b are not energized.

Figure 21B:
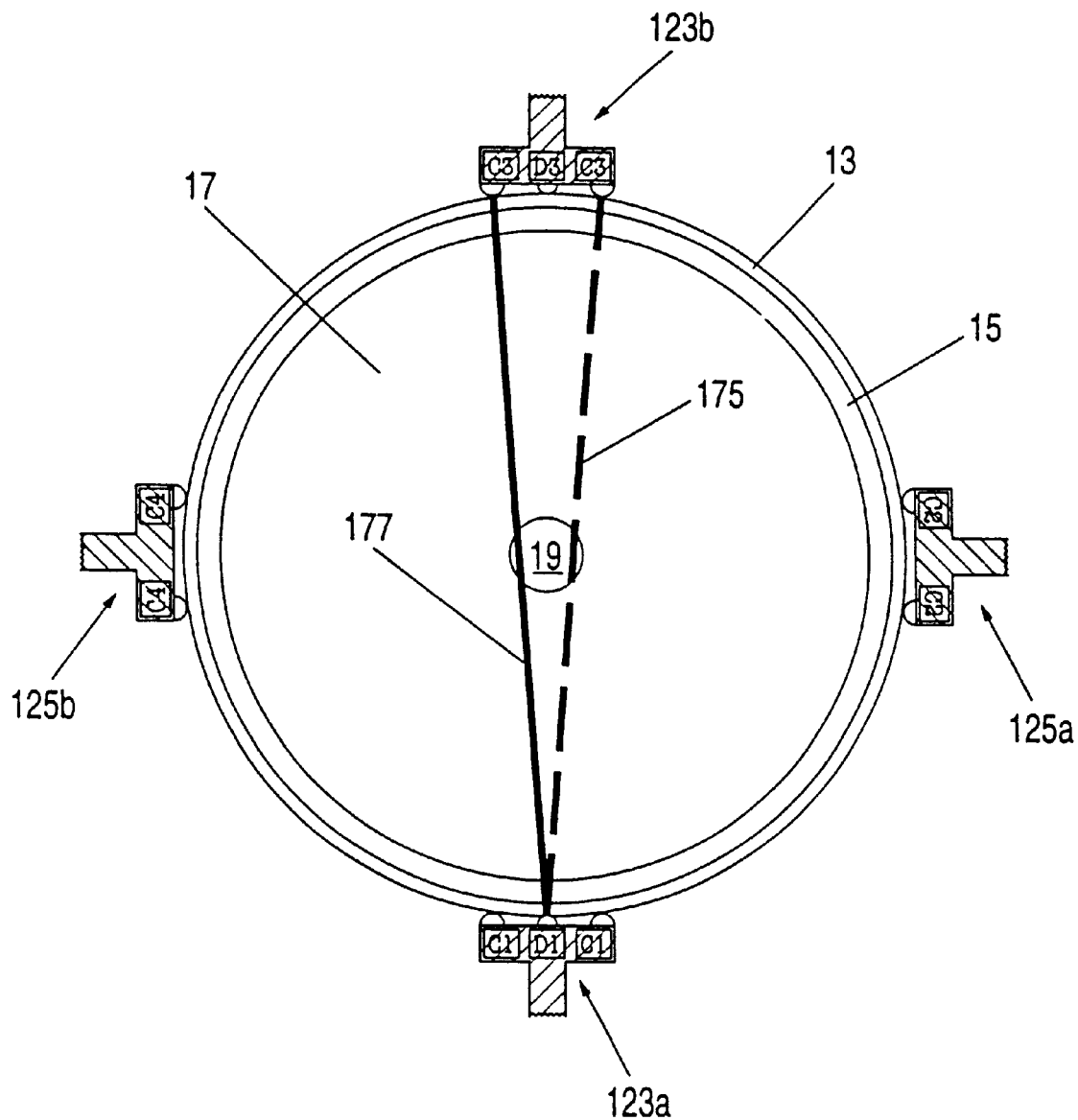

Spectra in the region from 1100 to 1400 nm does not require compensation for skin differences because the affects of melanin and other skin components are not present at wavelengths above 1100 nm. Thus, maximizing the amount of light into the finger while also maximizing the amount of information recorded from the finger is desired and achievable. This can be performed by energizing (again in accordance with Hadamard transform optical coding techniques) those LEDs on the 1100 to 1400 nm range on probe 123b. The light emitted from such LEDs is recorded by detector 135/123a. FIG. 21B illustrates this concept, with lines 175 and 177 representing a couple of the theoretical pathlengths.

Figure 21C:
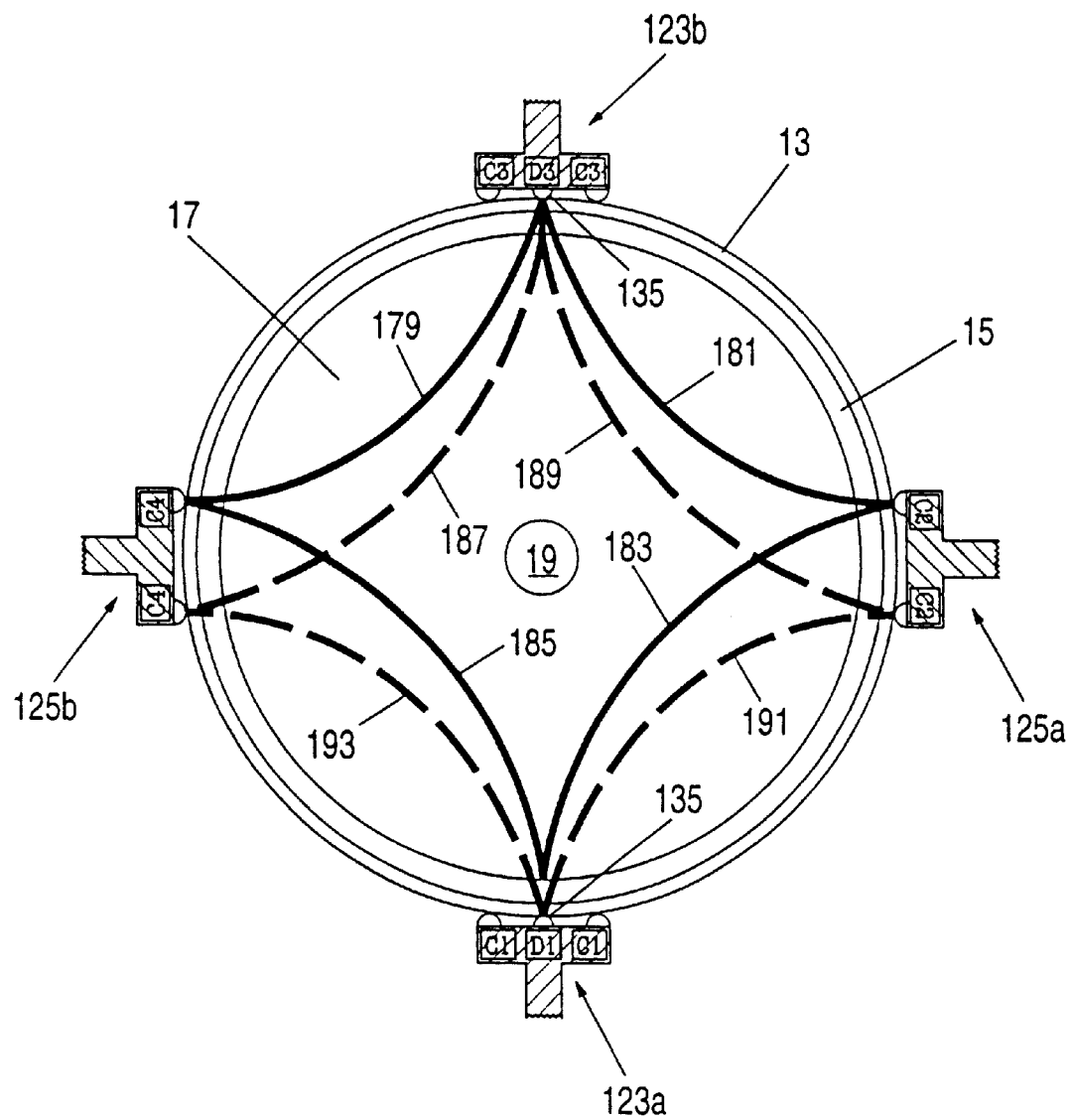

As previously discussed, light propagation through tissue at wavelengths longer than 1400 nm becomes heavily influenced by water absorbance. Measurement of wavelengths between 1400 and 1550 nm can be performed by energizing the LEDs in probes 125a and 125b. The light emitted from these LEDs will be simultaneously measured by detectors 135/123a and 135/123b. FIG. 21C illustrates this arrangement with representative theoretical light paths 179, 181, 183, 185, 187, 189, 191 and 193.

The end result of the preceding process is measurement of the spectral data from 400 to 1550 nm in the least possible time, with the highest possible signal-to-noise ratio and containing the spectral information necessary for analyte measurement. The use of multiple detectors and light sources will improve the signal-to-noise ratio of the recorded data for a given measurement time due to the ability to signal average two measurements simultaneously, and the ability to use Hadamard transform techniques.

Figure 22:
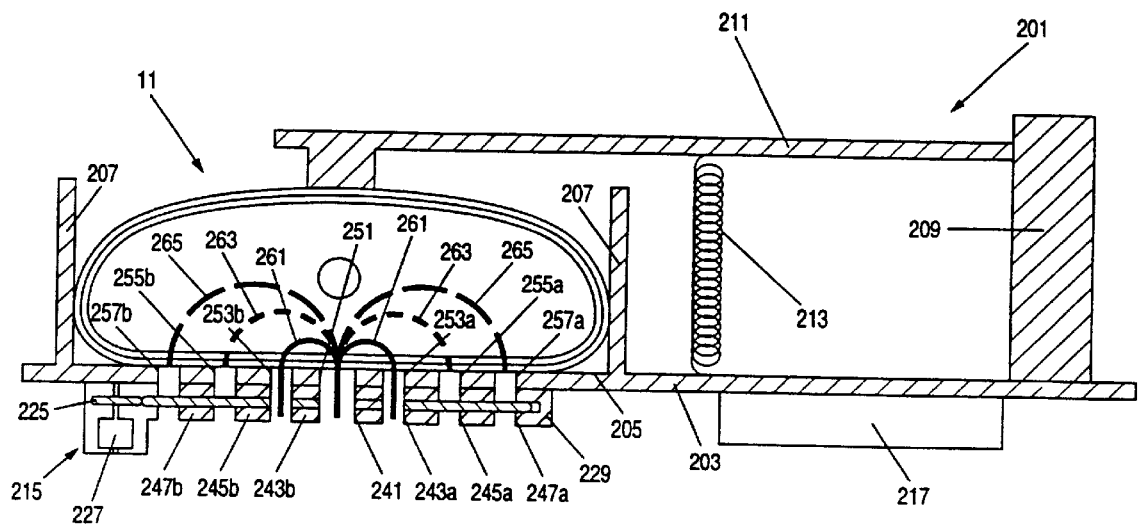
FIG. 22 illustrates a partial transmission finger sampling device.
Figure 23:
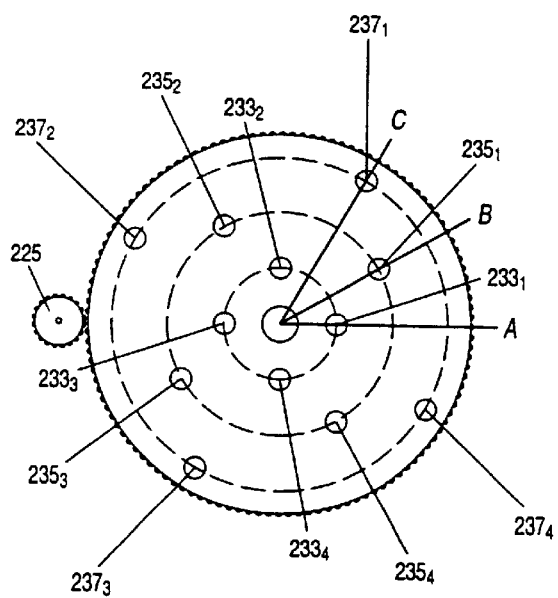
FIG. 23 is a bottom view of the shutter control of FIG. 22.

FIGS. 22 and 23, similar to FIGS. 12 and 13, show finger/thumb sampling device 201 using partial transmission with path optimization by separation of the sources and detector. Sampling device 201 includes base 203 having a finger support surface 205, a pair of guide rails 207 (for positioning finger/thumb 11) and a post 209. Device 201 also includes an arm 211 (which is hinged to post 209 and biased toward surface 205 by spring 213), shutter control 215, and temperature control device 217. Shutter control 215 includes a rotating disc 221 (having gear teeth 223 on the perimeter thereof), gear 225 and motor 227. Temperature control 217 includes an electrical heating pad, a temperature sensing device (e.g., a thermocouple) and associated conventional electronics (all not illustrated).

Disc 221, which is supported by housing 229 in any convenient manner (not shown), has a plurality of openings (typically circular) 231, $233_{1-4}$, $235_{1-4}$, and $237_{1-4}$, as best illustrated in FIG. 23. Housing 229 includes a series of openings 241, 243a and 243b, 245a and 245b, and 247a and 247b, which are always aligned with, respectively, openings (251, 253a and 253b, 255a and 255b, and 257a and 257b) provided in base 203.

In operation, light is introduced into finger/thumb 11 by fiber optic sources (not shown), the ends of which are received in openings 243a, 243b, 245a, 245b, 247a, and 247b. The distances between the fiber optic sources and the fiber optic detector (also not shown) which is received in opening 241 is optimized for pathlength for the reasons discussed above. The light introduced into finger/thumb 11 from the fiber optics received in openings 243a and 243b is partially transmitted with an average pathlength of 0.5 to 3 mm, as illustrated by theoretical paths 261. When these fibers are emitting light, the detector fiber receives light from 700 and 2400 nm. Openings 245a/255a and 245b/255b are separated from aligned openings 241/231/251 by a greater distance, to optimize the pathlength 263 for recording wavelengths in the 1400 to 2000 nm region. When this second set of fibers are emitting light, the majority of the light received by the detector fiber will be in the wavelength region from 700 and 2000 nm. Openings 247a/257a and 247b/257b are at the greatest distance from detector opening 241/231/251 and, thus, have the longest average pathlength 265. Fibers coupled to these source openings enable the measurement of wavelengths between 700 and 1400 nm. By placement of the source fibers and detector fiber on the same side of the finger/thumb the influence of finger thickness on the resulting spectral data is minimized. By reducing the influence of finger/thumb thickness, between patient differences are minimized and more accurate analyte measurements can be made.

In operation only those fibers at a given distance will emit light into finger/thumb 11 at a given time. Shutter system 215 controls which fibers are illuminating finger/thumb 11 at any one time. The blocking or passage of light is controlled by disk 221 and the angular orientation of openings $233_{1-4}$, $235_{1-4}$, and $237_{1-4}$ relative to each other. Central opening 231 allows transmission of light at all times. In operation disk 215 is rotated to position A, B, or C. In position A, disk 215 allows illumination of the finger by fibers connected to openings 243a and 243b. In FIG. 22 the disk is shown in position A and shows the complete propagation of light via path 261. If disk 215 is rotated to position B, the light would follow paths 263, as shown by the dotted lines. Rotation of disk 215 to position C would enable light to travel paths 265, as shown by the dashed lines. Thus, the use of the rotating disk forms a simple reliable shutter system to enable introduction of the light in a easily controlled manner.

In addition to pathlength optimization for the various wavelengths, the sampling device shown in FIGS. 22 and 23 is thermostated to control finger temperature. Control of the sampling devices temperature is performed by temperature control device 217 (including a heating pad, a temperature sensing device, typically a thermocouple, and associated electronics). The temperature control unit 217 is attached to plate 203.

With reference to FIG. 22, the tissue, typically a finger or thumb, is compressed firmly against surface 205 by arm 211 and spring 213. Compression of the finger with approximately 1 kg/cm$^2$ will, as discussed previously, minimize the influence of arterial pulsation in the optical sampling area. This force is not so extreme as to be painful to the patient. Other methods can be used to remove arterial pulsations, such as finger cuffs which are inflated to a pressure which occludes arterial pulsations. However, this cuffing technique has not proven as desirable, as application of force on the finger reduces movement of the tissue relative to the sampling device.

Previous configurations (except the embodiment of FIGS. 18–21) have involved the use of one detector, one wavelength separating device (e.g. AOTF, grating, etc.) and multiple sources. FIGS. 24, 25, 26 and 27 illustrate sampling configurations which utilize one source, multiple detectors, and multiple wavelength separating devices.

Figure 24:
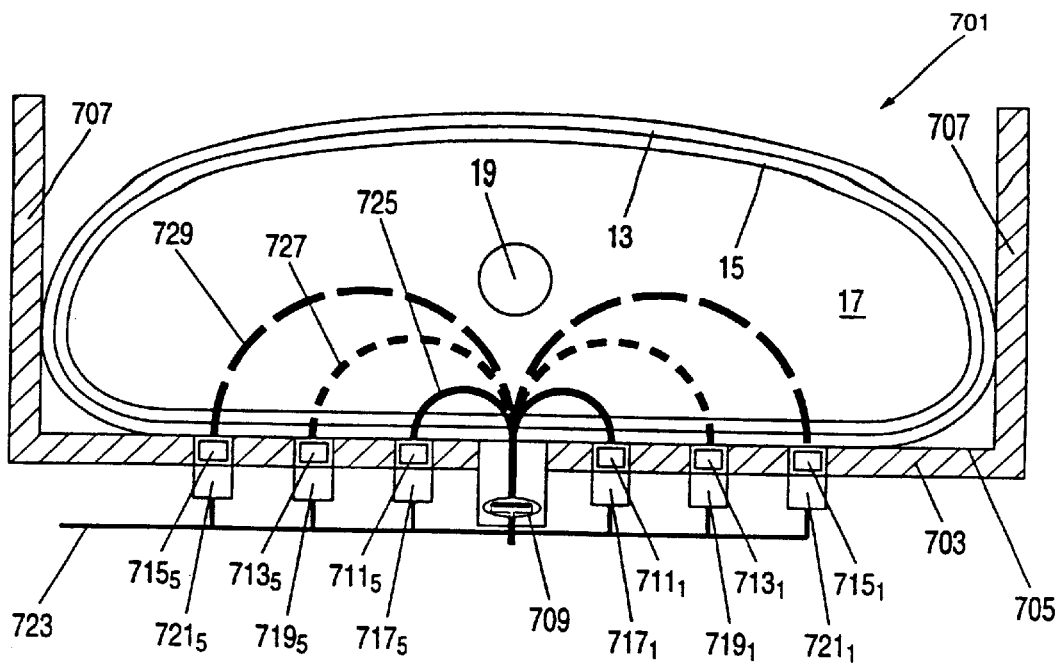
FIG. 24 illustrates a partial transmission finger sampling device with a single source and multiple detectors.
Figure 25:
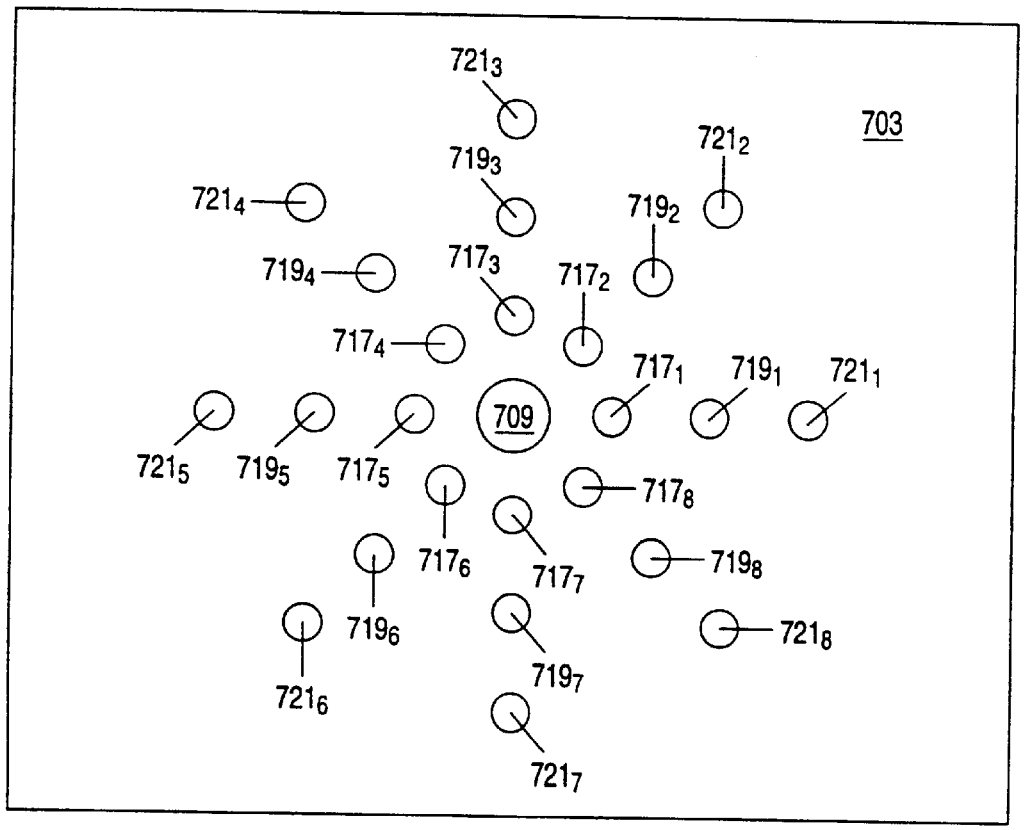
FIG. 25 is the bottom view of the device illustrated in FIG. 24.

FIGS. 24 and 25 illustrate sample device 701, which includes a base 703, a finger support surface 705, and a pair of guide rails 707 for positioning finger/thumb 11. Like sampling device 201, but not illustrated, device 701 includes an arm, secured to a post and biased into engagement with the finger/thumb 11 by a spring. Positioned within base 703 is a single broadband light source 709 and 24 band-pass optical filters, 6 of which are illustrated in FIG. 24 (i.e., $711_1$, $711_5$, $713_1$, $713_5$, $715_1$, and $715_5$). These band-pass optical filters are constructed of specially coated glass which permits only the preselected wavelengths (either a single wavelength or a band of contiguous wavelengths) to pass. The other wavelengths are attenuated or not permitted to pass through. Each of the band-pass filters is coupled to a detector (i.e., $717_{1-8}$, $719_{1-8}$, and $721_{1-8}$). The detectors are electrically connected an analog to digital converter via wires such as indicated by 723 in FIG. 24.

In operation, broadband source 709 is energized with some of the light partially transmitted through finger/thumb 11, as illustrated, by traces 725, 727 and 729. The light then passes through the band-pass optical filters which reduce the broadband light into preselected wavelengths (as indicated above). These discrete wavelengths are then detected on the detectors $717_1$–$721_8$. With the use of 24 detectors, 24 wavelengths are measured. The actual measurement of these intensity values could be one at a time, through standard sample and hold electronics or by Hadamard transform optical coding. Although 24 detectors are illustrated, the number could be increased or decreased. This design is based on the fact that accurate analyte measurement can be obtained with a certain number of preselected wavelengths. See FIG. 8.

Figure 26:
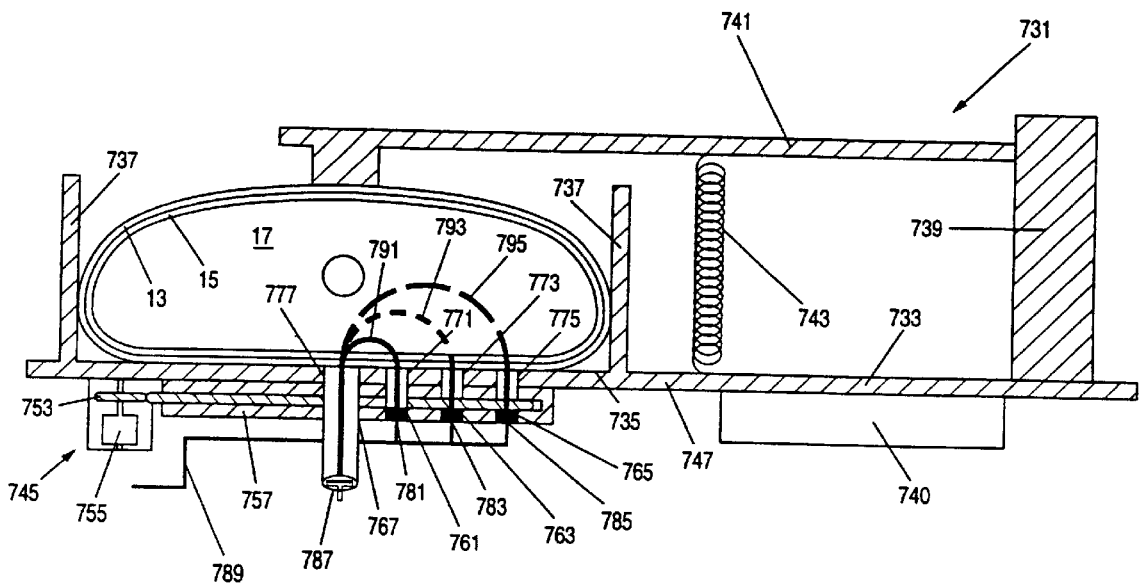
FIG. 26 illustrates an alternate partial transmission finger sampling device, with a single source and multiple detectors.
Figure 27:
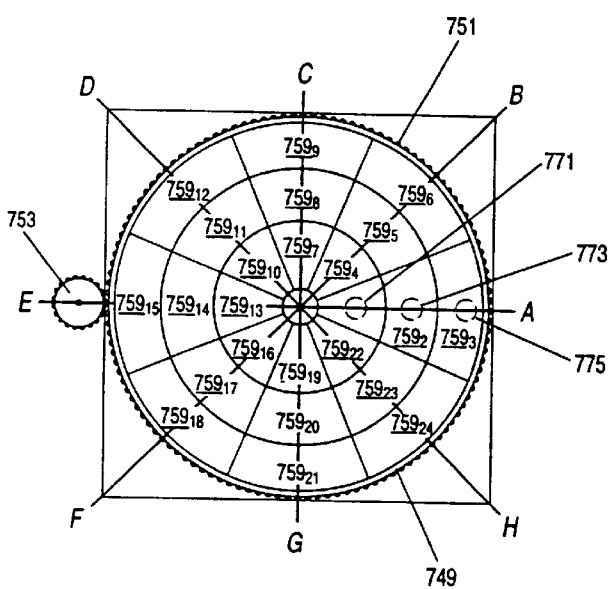
FIG. 27 is a view of FIG. 26 taken along lines X—X.

Sampling device 731, illustrated in FIGS. 26 and 27, includes a base 733, having a finger support surface 735, a pair of guide rails 737, and a post 739. Device 731 also includes a temperature control device 740, and an arm 741, which is hinged (not shown) to post 739 and biased toward surface 735 by spring 743. Filter wheel assembly 745, which is secured to surface 747 of base 733, includes a rotating filter wheel 749 (having gear teeth 751 on the perimeter thereof), gear 753, and stepper motor 755. Filter wheel 749, which is supported by housing 757 in any convenient manner (not shown) is provided with 24 band-pass filters $759_{1-24}$, each of which passes wavelength subsets ($\lambda_1, \lambda_2, \lambda_3 \ldots \lambda_{24}$). Housing 757 also includes openings 761, 763 and 765 (which are aligned with, respectively, openings 771, 773 and 775 in base 735) and central opening 767 (which is aligned with opening 777 in base 735). As illustrated, detectors 781, 783 and 785 are positioned in the lower end of openings 771, 773 and 775. Light source 787 is positioned relative to aligned openings 767, 777. Detectors 781, 783 and 785 are connected to an analog to digital converter via signal line 789.

In operation, light is introduced into finger/thumb 11 via broadband source 787 via a light pipe, a portion of which is partially transmitted as indicated by paths 791, 793 and 795. Light with a wavelength $\lambda$, which traverses path 791 passes through filter $759_1$, and is detected by detector 781. Similarly, light with a wavelength $\lambda_2$, which traverses path 793, passes through band-pass filter $795_2$ to detector 783. Finally, light with a wavelength $\lambda_3$, which traverses path 795, passes through band-pass filter $795_3$ to detector 785. As filter wheel 749 has eight discrete positions (i.e., A–H), once the intensities of wavelengths $\lambda_1$, $\lambda_2$, and $\lambda_3$ have been measured, stepper motor rotates wheel 749 from the position illustrated in FIG. 27 to the position where position B is aligned with detectors 781, 783 and 785. In this position the intensities of wavelengths $\lambda_4$, $\lambda_5$ and $\lambda_6$ are then measured. Wheel 749 is rotated through the remaining positions until all 24 wavelengths are measured.

Figure 28:
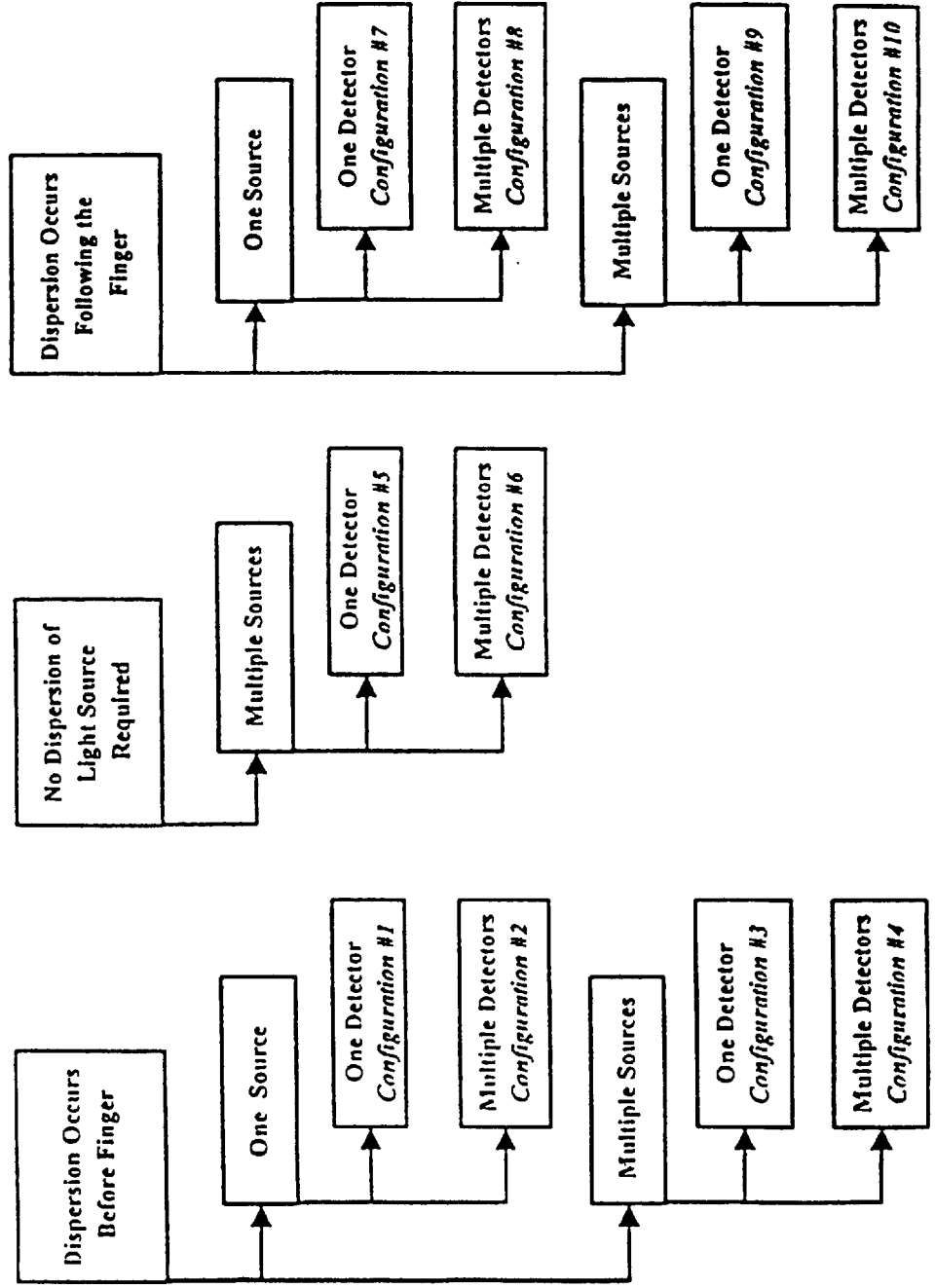
FIG. 28 is a block diagram showing three major instrument categories based on the disclosure herein.

Regardless of the exact finger sampling device used, each enables optimization of the path used for optical sampling vis-a-vis the light propagation characteristics of the measured wavelengths. The associated instrumentation needed to generate and subsequently measure these "optimized" wavelengths can take a variety of forms. FIG. 28 illustrates in a box diagram the general configurations that such instrumentation can take. The three major categories involve dispersion options followed by source options, and finally those options available for detectors. The ten configurations are discussed below.

Figure 29:
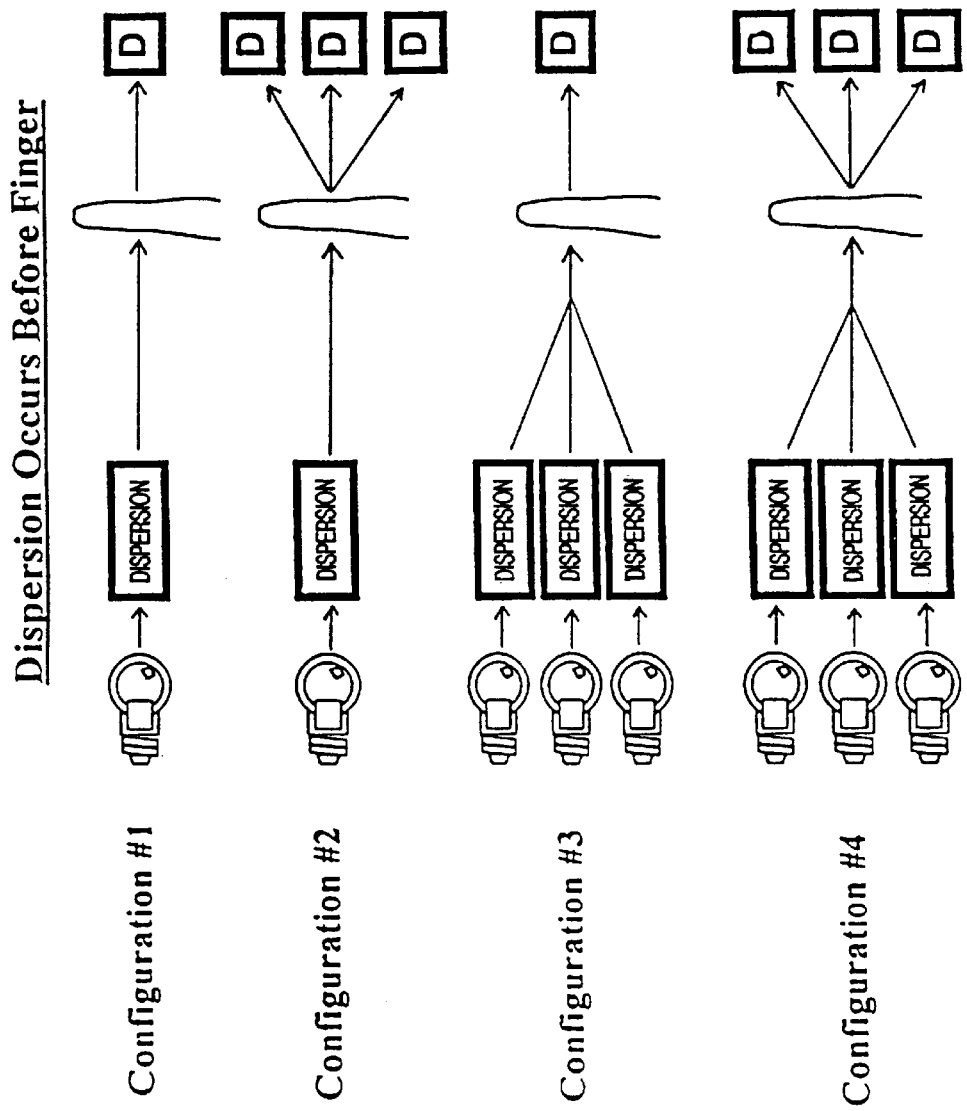
FIG. 29 is a schematic diagram of those instrument embodiments wherein dispersion of the light occurs prior to irridation of the finger.
Figure 35:
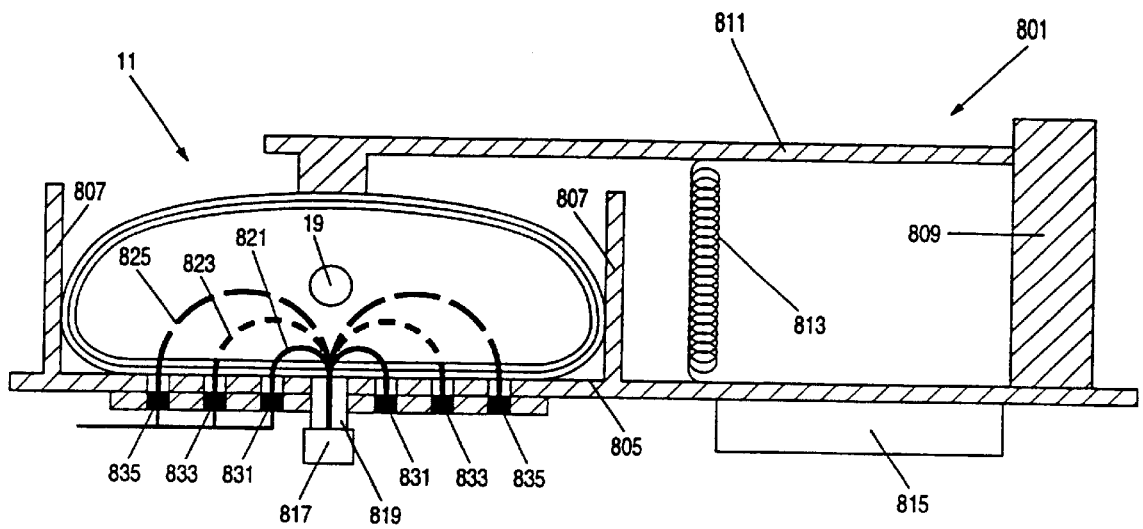
FIG. 35 illustrates yet another partial transmission finger sampling device, with a single source and multiple ring detectors.
Figure 37:
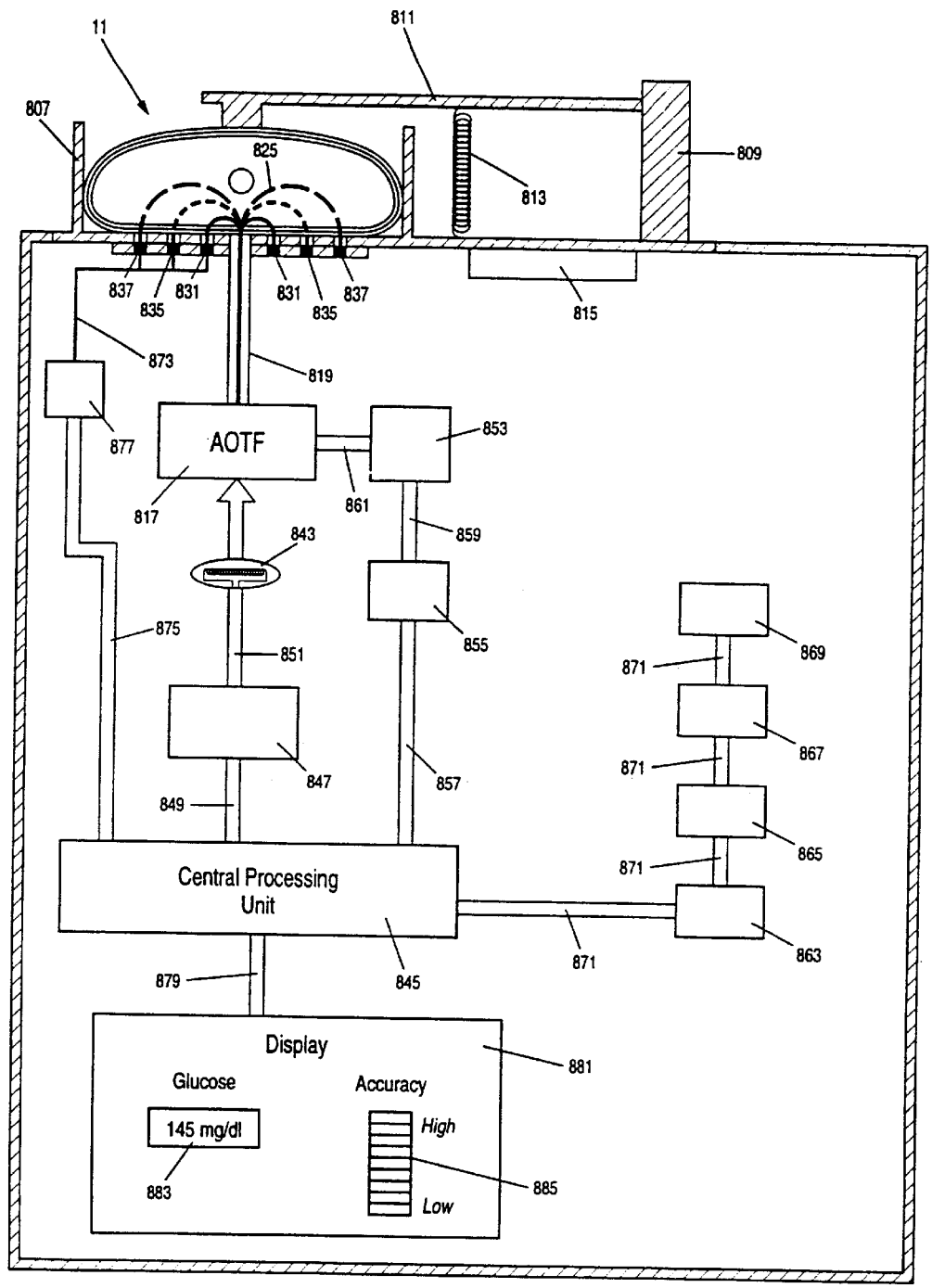
FIG. 37 is a schematic of a noninvasive analyte monitor using the device of FIGS. 35 and 36.

FIG. 29 schematically illustrates Configurations 1 through 4, where the light is dispersed or separated before it interacts with the finger. In all cases the light sources generates light with a band width broader than desired for the noninvasive measurement. In most cases the light source will be a broadband light source such as a tungsten halogen lamp. The broadband light is subsequently separated or dispersed and only the wavelengths of interest interact with the finger. The dispersion of the light can be performed by a number of devices. Dispersion devices in common use are AOTFs, Fourier transform interferometers, and filter wheels. FIGS. 35 and 37 illustrate the use of an AOTF to disperse the light before it interacts with the tissue. The light of FIGS. 35 and 37 then propagates through the tissue and is subsequently detected by multiple detectors. This corresponds to Configuration 2 in FIG. 29.

Figure 30:
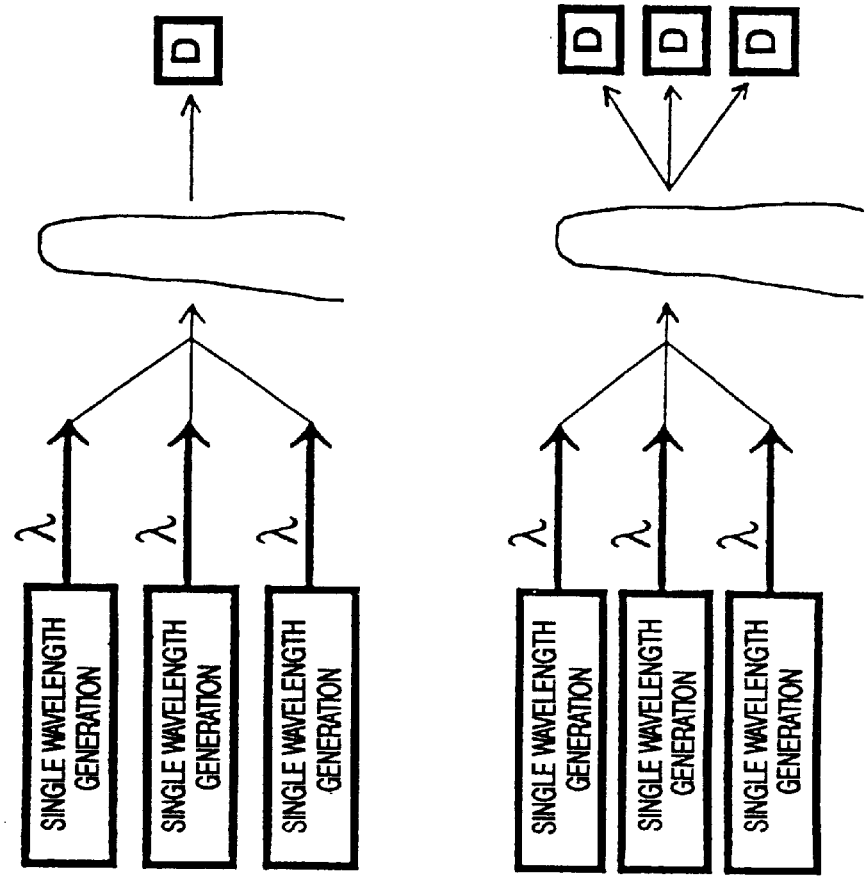
FIG. 30 is a schematic diagram of those instrument embodiments wherein no dispersion of the light is required.
Figure 34:
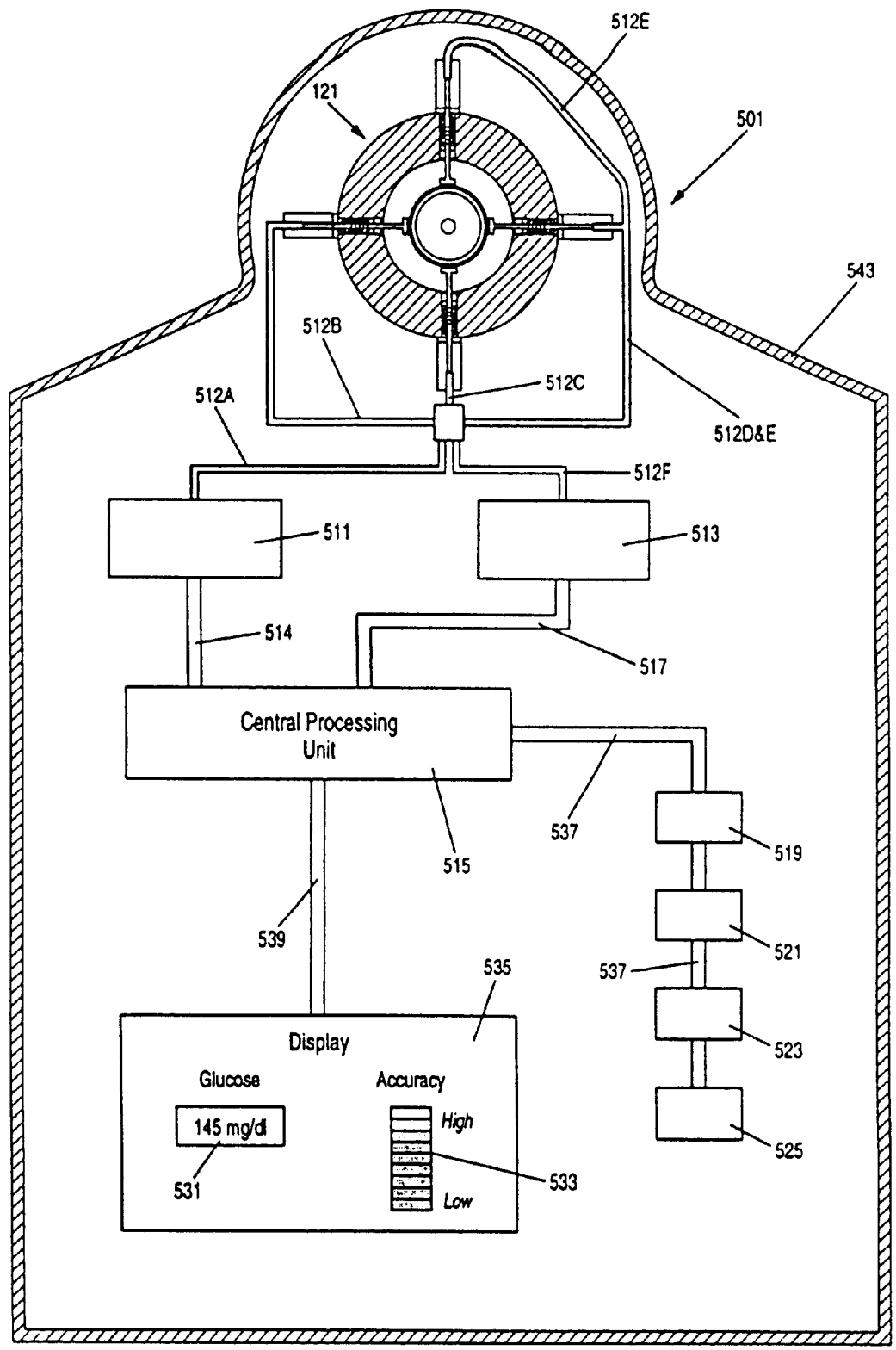
FIG. 34 is a schematic of a noninvasive analyte monitor using light emitting diodes.

FIG. 30 schematically illustrates Configurations 5 and 6, where the light source is capable of emitting light of a narrow bandwidth and subsequent dispersion of the light is not necessary. Some light sources having these characteristics are light emitting diodes, lasers of all types, and tunable lasers. Although a tunable laser is a single unit, it is considered as multiple sources in this description. FIGS. 18 and 34 illustrate Configuration 6 and describe a noninvasive measurement device incorporating multiple sources and multiple detectors.

Figure 32:
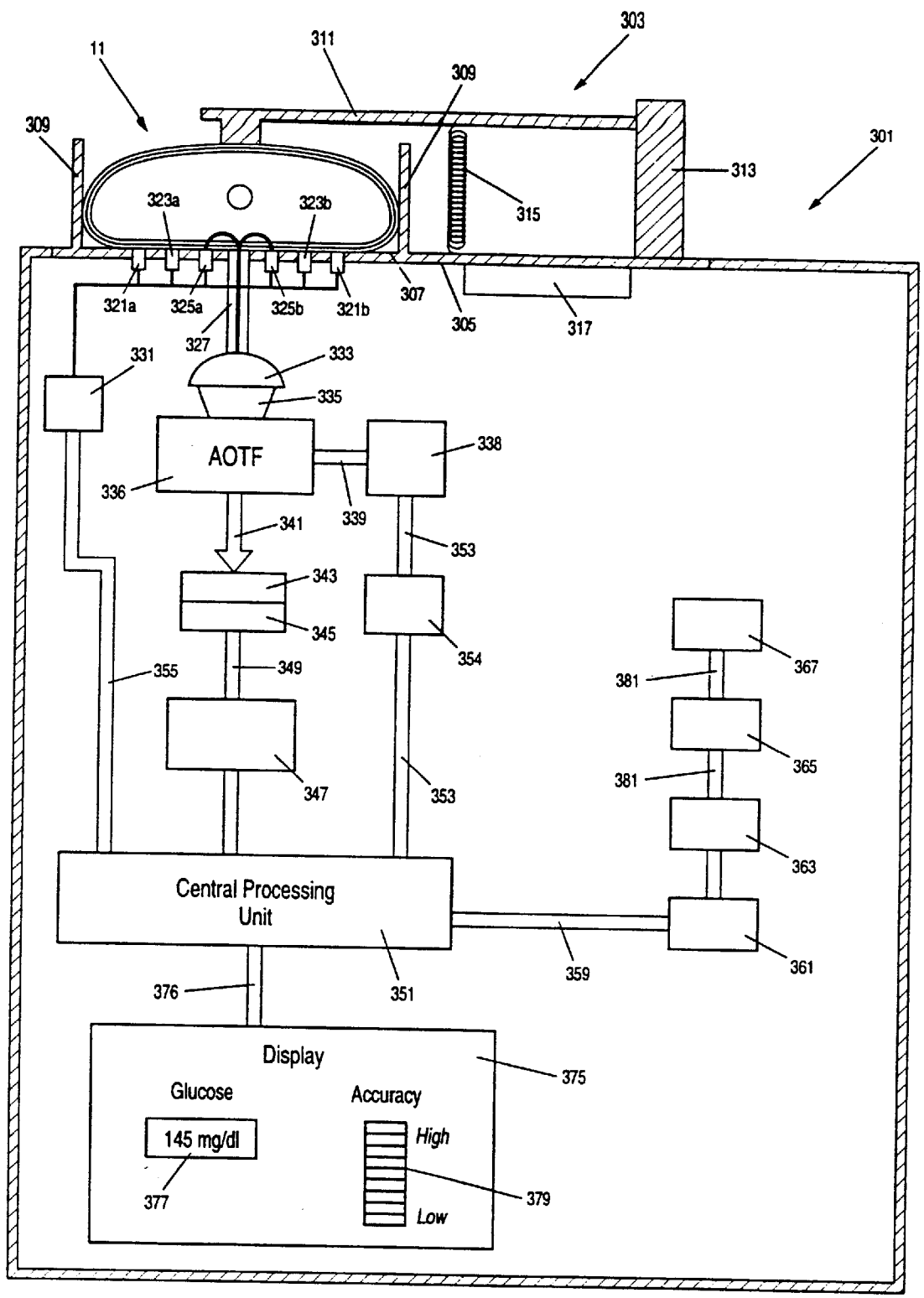
FIG. 32 is a schematic of a noninvasive analyte monitor using small multiple tungsten-halogen light sources.
Figure 33:
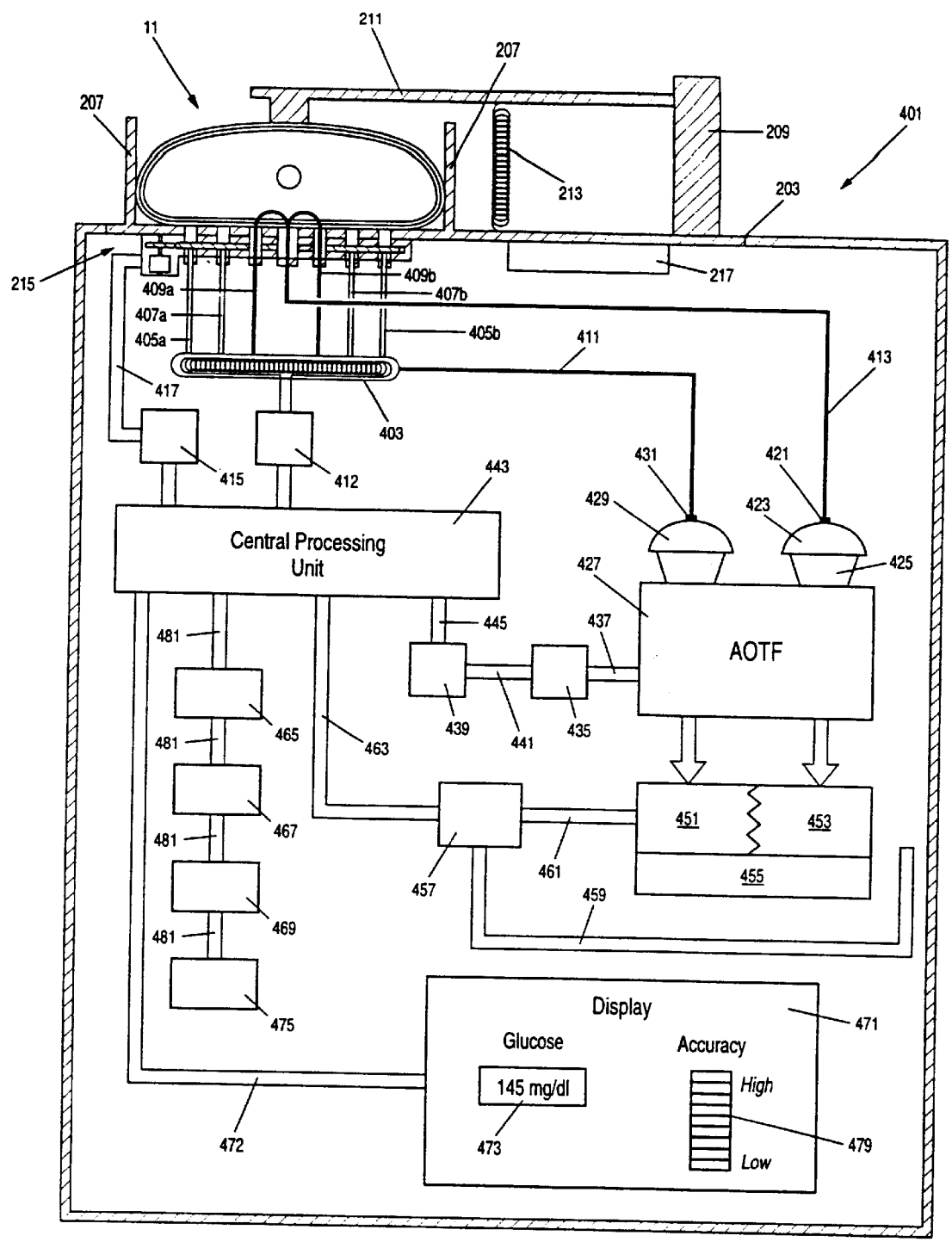
FIG. 33 is a schematic of an alternate noninvasive analyte monitor using a single broadband light source and fiber optics.

FIG. 31 schematically illustrates Configurations 7 through 10, where the light is dispersed following its interaction with the finger. The light source emits light of a bandwidth greater than desired for noninvasive measurement and subsequent separation of the light is required. The separation of the light can be performed by numerous commercially available components. FIGS. 24–27 illustrate Configuration 8 wherein the dispersion of light is performed by selective optical filtering. FIG. 32 illustrates Configuration 9 wherein the dispersion of the light is performed by an AOTF following interactions with the finger. FIG. 33 illustrates a variation of Configuration 10 wherein the light is separated by an AOTF. Two detectors are employed in order to record both the light having propagated through the finger as well as the intensities of the light source via a background fiber.

As one skilled in the art will recognize an infinite number of instrument configurations can be realized for measurement of the appropriate spectral information. For clarity four instrument examples are illustrated and their operation described.

FIG. 32 illustrates a noninvasive analyte monitor 301 using multiple small tungsten-halogen light sources. Again, partial transmission with separation of the detector and sources for optimization of the various paths within the finger is employed. Monitor 301 includes a finger sampling device 303 which, like sampling device 201, includes a base 305, finger support surface 307, a pair of guide rails 309 (for positioning finger or thumb 11), arm 311, support arm post 313, spring 315 for biasing finger/thumb 11 into engagement with surface 307, and temperature control 317.

The light sources 321*a* and 321*b*, 323*a* and 323*b*, and 325*a* and 325*b* and detector light pipe 327 are received in base 305 to make contact with finger/thumb 11 in a repeatable manner, as illustrated. Light sources 321a–325b are connected to (via signal line 330) and controlled by conventional electronics in housing 331. As those skilled in the art will appreciate, those light sources at a given distance from the detector light pipe 327 will be energized simultaneously. Thus, for measuring long path wavelengths, sources 321a and 321b will be on at the same time. The light enters the tissue of finger/thumb 11 and propagates through, with a portion exiting into light pipe 327. Light pipe 327 is composed of fused silica and serves to transport the light from the finger/thumb 11 to imaging optics 333 which, in turn, directs the light 335 onto the aperture of AOTF crystal 336.

The specific wavelength or wavelengths transmitted by AOTF 336 is determined by the rf signals introduced onto the crystal by tunable rf source 338 via signal line 339. As those skilled in the art will appreciate, a piezoelectric crystal ($LiNbO_3$) is bonded to the $TeO_2$ crystal on a specific crystal face to inject an acoustic wave in the required direction. The light 341 exiting AOTF 336 is detected by detector 343 which, in the preferred embodiment, is a thermoelectrically cooled Indium Gallium Arsenide detector. Other suitable detectors (such as InSb, Lead Sulfide and Germanium/Silica) may also be used. Thermoelectric cooling is performed by cooler 345. The resulting analog signal from detector 343 is communicated to A/D converter 347 by signal line 349. Central processing unit 351 ensures that the intensity seen by detector 343 is within its linear dynamic range, via pre-established intensity limits. If the intensity is not within range then a signal is sent to rf source 338, via signal line 353, to increase or decrease the rf power to AOTF crystal 336 until the intensity observed by detector 343 is within its linear operating range.

Figure 8:
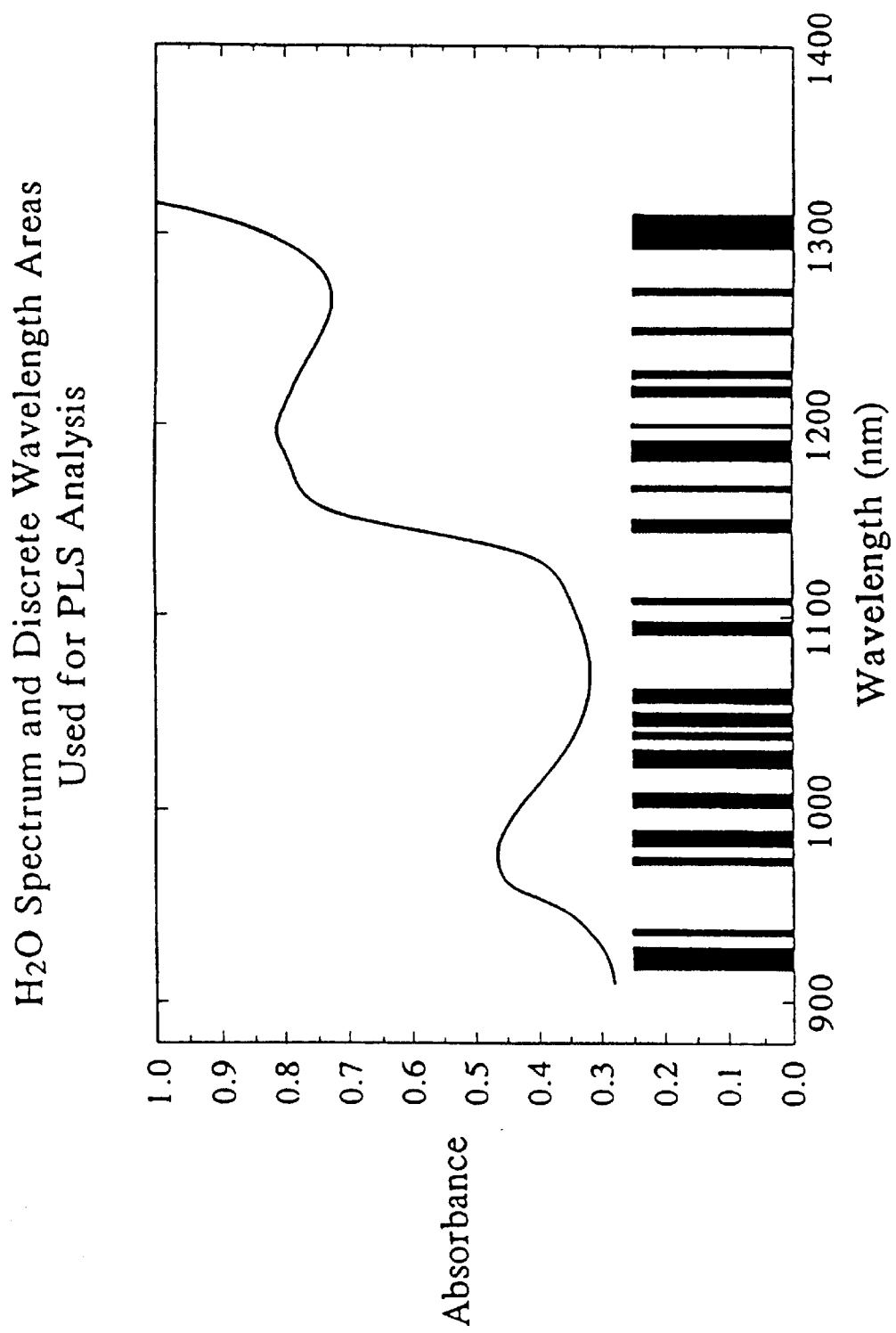
FIG. 8 is a plot of the water spectrum from 900 to 1300 nm, together with discrete glucose measurement bands (Note: the height of the discrete measurement bands is arbitrary)

With reference to FIG. 8, some wavelengths need to be measured at relatively high resolution (i.e. narrow bandwidth), while some can be measured at low resolution. By introduction of one or several rf frequencies the bandwidth of the light transmitted by AOTF 336 can be altered. The AOTF driver electronics 354, connected between central processing unit 351 and rf source 338, will be instructed by central processing unit 351 to allow measurement of the exact frequencies needed, at the resolution needed and at the appropriate signal-to-noise ratio. The wavelength transmitted and subsequently recorded is controlled by the frequency of the rf signal applied to AOTF crystal 336. The resolution can be decreased by simultaneous introduction of several rf frequencies onto AOTF crystal 336. The signal-to-noise ratio can be controlled by the length of time a specific wavelength is recorded.

After a given wavelength or wavelengths are recorded, central processing unit 351 generates a signal to cause tunable rf source 338 to change the frequency being generated, and the next wavelength(s) is (are) recorded. Following measurement of all wavelengths using a given source-detector configuration (e.g., 321a and 321b/327), central processing unit 351 signals, via signal line 355, source driver electronics 331 to switch off the current to sources 321a and 321b, and to turn on sources 323a and 323b. The process is then repeated, and repeated again for sources 325a and 325b.

The wavelength intensity values from A/D converter 347 are communicated to central processing unit 351 and then transmitted via signal line 359 for storage in memory storage unit 361. Following measurement of all necessary wavelength intensity values in the manner set forth above, all these intensity values are processed by spectral processing algorithms stored in module 363 to produce a processed spectra, such as shown in FIG. 11. The resulting processed spectra is devoid of or has minimal patient to patient differences and is ready for quantitative analysis. Quantitative analysis of the processed spectra is preformed by central processing unit 351 in conjunction with the multivariate calibration model and algorithms stored in module 365 and the processed spectra stored in memory storage unit 361. The analysis process determines the concentration of the analyte. The multivariate methodology used is disclosed in U.S. Pat. No. 4,975,851, the disclosure of which is incorporated herein by reference. The concentration value is subsequently transmitted via signal line 376 for display by unit 375. For example, glucose concentration would be displayed in mg/dl units on screen 377.

Concurrent with the concentration determination, processed spectra is examined to determine if it is an outlier. Outliers are spectra not representative of the calibration samples. The outlier detection methods used are also disclosed in U.S. Pat. No. 4,975,851. In simple terms, if the spectra is unique or dissimilar from those used to develop the model then the accuracy of the measurement is not well defined. The determination of measurement accuracy is performed by central processing unit 351 while using the processed spectra stored in memory storage unit 361 and the outlier detection algorithms stored in module 367. The result of the analysis can be displayed by unit 375 as a bar graph 379 indicating accuracy. Memory storage unit 361 and modules 363, 365 and 367 are interconnected by signal line 381.

FIG. 33 illustrates the major components of a robust noninvasive glucose monitor 401 employing a broadband light source and fiber optics. The optical sampling of finger/thumb 11 is performed with the same structure and in the same manner as previously discussed in reference to FIGS. 22 and 23. The optical illumination is performed by a broadband light source 403, typically a tungsten halogen source, which is coupled by any suitable conventional method to a group of source fibers 405a and 405b, 407a and 407b, and 409a and 409b. Source 403 is also coupled to background fiber 411 for the reasons explained below. The filament used in source 403 is elongated, so the distance from the filament to each fiber is constant. Illumination of source 403 is controlled by electronics 412. The source fibers are connected from source 403 to shutter box 215, as previously described in connection with FIGS. 22 and 23. In operation, shutter box 215 allows light from fibers located at the same distance from the detector to be simultaneously transmitted into finger/thumb 11. As shown, illumination of finger/thumb 11 is with those fibers closest to the detector fiber 413. As before, rotation of disk 215 is controlled by motor 227 which, in turn, is coupled to shutter driver electronics 415 via signal line 417.

The light having propagated through finger/thumb 11 is collected by detector fiber 413 which may be a single fiber or a fiber optic bundle. Detector fiber 413 is connected, by fiber coupler 421, to imaging optics 423, which focuses the light 425 onto a portion of the aperture of AOTF crystal 427. AOTF crystal 427 is, preferably, made of $TeO_2$ and has an aperture of, approximately, 0.5 cm.×0.5 cm.

Background fiber 411 is coupled to light source 403 in a conventional manner (not shown), such as used for source fibers 405a–409b. At its opposite end, fiber 411 is connected onto imaging optics 429 by coupler 431. The light from both detector fiber 413 and background fiber 411 are imaged simultaneously onto the aperture of AOTF 427. The optical transmission properties of AOTF 427 are controlled by the rf signals incident to the crystal, which are produced by radio frequency source 435 coupled to the piezoelectric crystal on AOTF 427 by signal line 437. Rf source 435 is, in turn, controlled by driver electronics 439 via signal line 441. Electronics 439 are controlled by central processing unit 443 via signal line 445.

The desired wavelengths of light are transmitted through AOTF 427 and are incident upon two detectors 451 and 453, which are matched so as to have similar response curves. In the preferred embodiment the detectors are composed of Indium Gallium Arsenide and are thermoelectrically cooled by thermoelectric cooler 455 to improve performance. The two detectors receive the light from AOTF 427 and convert the light intensity into a series of electrical signals indicative of the light transmitted by, respectively, background 411 and detector 413 fibers. The electrical signals which correspond to the intensity values at the detector are transmitted to electronics 457 via signal lines 459 and 461. Within electronics 457 is an A/D converter and computational hardware that ensures that both detectors are functioning within their respective operational range. If the intensity of the light received from AOTF 427 is not within the established linear operating range of the detectors, the rf power incident onto AOTF 427 is changed until the response is within such range. For each wavelength recorded (for both background 411 and detector fiber 413), rf source 435 generates a different rf frequency.

The digital numbers corresponding to the intensity values at each wavelength from both detectors 451 and 453 are communicated from electronics 457 to central processing unit 443 via signal line 463. The digital intensity values are subsequently stored in memory module 465 until all wavelength intensities have been recorded. Following measurement of all necessary wavelength intensity values, these values are processed by spectral processing algorithms stored in module 467. The result is a final processed spectra, such as previously illustrated in FIG. 11. The intensity values from the proposed spectra are also stored in memory module 465 for subsequent processing. The final processed spectra is the spectral data which has been processed to minimize between patient differences and is now ready for quantitative analyte measurement. Quantitative analysis of the processed spectra is preformed by central processing unit 443 in conjunction with the multivariate calibration model and algorithms stored in module 469 and the stored processed spectra stored in module 465. The analysis process, carried out in the manner set forth in U. S. Pat. No. 4,975,581, determines the analytes concentration. The concentration value is subsequently displayed by unit 471, connected to central processing unit 443 via signal line 472. For example, glucose concentration would be displayed in mg/dl units by display 473. Concurrent with the concentration determination, the processed spectra is examined to determine if it is similar to those used to generate the calibration model. If the spectra is unique or dissimilar from those used to develop the model then the accuracy of the measurement is poorly defined. The determination of measurement accuracy is performed by central processing unit 443 while using the processed spectra stored in module 465 and outlier detection algorithms stored in module 475. The result of this analysis is displayed on accuracy bar graph 479. Central processing unit 443, and modules 465, 467, 469 and 473 are interconnected by signal lines 481.

Robust noninvasive monitor 501, FIG. 34, is based on finger sampling device 121, illustrated in FIGS. 18–20. The LEDs and detectors on finger sampling device 121 are controlled in the manner as described in reference to FIGS. 21A, 21B and 21C. The activation of the LEDs is controlled by LED driver electronics 511 via signal lines 512A, B, C, D, and E. The electrical signals from the detectors are transmitted (via signal lines 512 B, C, D, E and F) to and processed by detector electronics 513. The resulting intensity values are communicated to central processing unit 515, via signal line 517, and subsequently stored in memory unit 519. Following completion of irradiation/measurement phase, the stored wavelength intensity values are processed by central processing unit 515. The spectral processing is performed as described in reference to FIGS. 32 and 33. The processing uses memory module 519, spectral processing module 521, multivariate model and algorithm module 523 and outlier detection module 525. The results of the spectral analysis are displayed on screen 531 and accuracy bar graph 533 of display unit 355. Modules 519, 521, 523 and 525 are connected to central processing unit 515 via signal lines 537. Display 535 is connected to central processing unit 515 via signal line 539. Driver electronics 511 is coupled to central processing unit 515 by signal line 541. All components are located in housing 543.

Whereas this preferred embodiment has focused on the use of LEDs, those skilled in the art will recognize that any single or selected wavelength emitting device could be used in a similar manner. For example, the LEDs could be replaced by a combination of a tungsten light source with a selective filter on the output side. It is also recognized that small diode lasers or other lasers could be used in place of the LEDs. Thus, the apparatus and associated methodology described in FIG. 34 is applicable to any light sources generating a discrete number of wavelengths.

Figure 36:
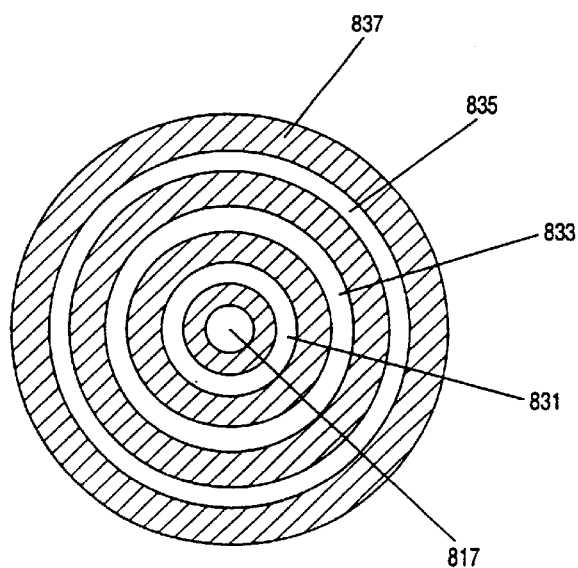
FIG. 36 is a planar view of the detector ring assembly of FIG. 35.

FIG. 35 is an illustration of a finger sampling device which utilizes a single broadband source which is transmitted through a wavelength separating device. Similar to previous ones, sampling device 801 includes a base 803, finger support surface 805, guide rails 807, post 809, hinged pressure arm 811, bias spring 813, and temperature control 815. Device 801 also includes a wavelength separating device 817, coupled to base 803 via light pipe 819. Preferably device 817 is an AOTF. However, a filter wheel or other device which has the ability to separate broadband light into specific wavelengths could be used. The specific wavelength that is emitted from device 817 is then partially transmitted through finger/thumb 11 as illustrated by traces 821, 823 and 825. After partial transmission through finger/thumb 11 the light at the selected wavelength is then detected by detector rings 831, 833 and 835 supported (by means not shown) on disc 837. FIG. 36 shows the equi-distant nature of the detector rings. Thereafter, the wavelength is changed and another specific wavelength is partially transmitted through finger/thumb 11. The process is repeated until all desired wavelengths are transmitted.

FIG. 37 illustrates the major components of a robust noninvasive glucose monitor 841 employing a single broadband light source and the sampling device of FIGS. 31 and 32. Monitor also includes broadband light source 843 coupled to source electronics 847 which are controlled by central processing unit 845 via electrical connections 849 and 851. AOTF 817 is, as with the embodiment of FIG. 28, coupled to central processing unit 845 via tunable rf source 853, AOTF driver electronics 855 and signal lines 857, 859 and 861. Also, as with the embodiment of FIG. 28, monitor 841 includes memory storage unit 863, module 865 (in which are stored spectral processing algorithms), module 867 (in which is stored the multivariate calibration model and spectral processing algorithms and outlier detection module 869. Memory unit 863 and modules 865, 867 and 869 are interconnected via signal line 871. Signals from detectors 831, 833 and 835 are transmitted to analog-to-digital converter 877. The digital values from converter 877 are transmitted to central processing unit 845 via electronic bug 875 and processed in the manner disclosed with monitor 301 (FIG. 31). The result of the analysis is transmitted via signal line 879 for display by unit 881 as a specific value on display 883 and a bar graph 885 indicating accuracy.

Whereas this specification has focused on the noninvasive measurement of glucose, those skilled in the art will appreciate that changes can be made to the preferred embodiment to measure other analytes. It is recognized that the wavelength region used for measurement will vary between the different blood analytes of interest. For example, acceptable accurate results for bilirubin and hemoglobin are possible through use of the 300–1000 nm region. Specifically, bilirubin has a significant absorption peak at approximately 454 nm and oxygenated hemoglobin has a peak at approximately 410 nm. Alcohol, another analyte of significant interest, has a sharp spectral absorbance at 1190 nm. Thus, the method of sampling and the associated optical instrumentation may be changed to optimize measurement accuracy for any number of analytes without affecting the scope of this invention.

Whereas the drawings and accompanying description have shown and described the preferred embodiment of the present invention, it should be apparent to those skilled in the art that various changes may be made in the form of the invention without affecting the scope thereof.

What I claim is:

1. A method of determining noninvasively an unknown value of a known characteristic, particularly the concentration of at least one analyte in tissue containing multiple spectral interferences, said method including the steps of:
   (a) providing at least one source of infrared energy having multiple wavelengths;
   (b) using at least one means for introducing said infrared energy into said tissue and at least one means for collecting said infrared energy to provide first and second optical paths of different lengths through said tissue;
   (c) measuring with at least one detector the intensities of at least some of said multiple wavelengths which have traversed said tissue through said first and second optical paths; and
   (d) calculating said unknown value by using said measured intensities from said first and said second optical paths, said calculating using said measured intensities from both optical paths to compensate for said spectral interferences in said tissue.

2. The method as set forth in claim 1, wherein said spectral interferences include but are not limited to differences in hydration, the amount of blood in said tissue, temperature differences, melanin differences, blood analyte concentration differences and epidermal differences.

3. The method as set forth in claim 1 wherein said wavelengths collected from said first path are different from the wavelengths collected from said second path.

4. In a method of determining noninvasively and in vivo one or more unknown values of a known characteristic, including the steps of irradiating human tissue with at least one source of infrared energy having at least several wavelengths in a given range of wavelengths so that there is differential absorption of at least some of said wavelengths by said tissue as a function of said wavelengths and said characteristic, said differential absorption causing intensity variations of said wavelengths, collecting with at least one detector at least some of said wavelengths that have traversed an average optical path through said tissue, and calculating said one or more unknown values of said known characteristic, the improvement comprising: positioning said at least one source and at least one detector relative to said tissue to provide at least first and second average optical paths through said tissue, said first path being different in length from said second path, and wherein said calculating uses intensities obtained from said first and second paths to compensate for spectral interferences.

5. The method as set forth in claim 4, wherein said range is between 400 and 2400 nm.

6. The method as set forth in claim 4, wherein at least one of said paths represents a partial transmission path through said tissue.

7. The method as set forth in claim 6, wherein said tissue is a finger and wherein said partial transmission path passes through the nail of said finger at least once.

8. The method as set forth in claim 4, wherein said tissue is irradiated by a plurality of sources of infrared energy.

9. The method as set forth in claim 4, wherein said wavelengths are collected by a plurality of detectors.

10. A method as set forth in claim 4 wherein some of said wavelengths collected from said first path and some of said wavelenght collected from said second path are the same.

11. In a method of determining nonivasively and in vivo one or more unknown values of a known characteristic, including the steps of irradiating human tissue with at least one source of infrared energy having at least several wavelengths in a given range of wavelengths so that there is differential absorption of at least some of said wavelengths by said tissue as a function of said wavelengths and said characteristic, said differential absorption causing intensity variations of said wavelengths, collecting with at least one detector at least some of said wavelengths that have traversed an average optical path through said tissue, and calculating said one or more unknown values of said known characteristic, the improvement comprising: positioning said at least one source and said at least one detector relative to said tissue to provide at least first, second and third average optical paths through said tissue, said fist, second and third paths being different in length from each other.

12. The method as set forth in claim 11, wherein said first path is for the wavelength sub-region of 2000–2400 nm, said second path is for the wavelength sub-region of 1400–2000 nm, and said third path is for the wavelength sub-region of 400–1400 nm.

13. The method as set forth in claim 12, wherein said first path has a length in the range of 0.5–3 mm, said second path has a length in the range of 3–7 mm, and said third path has a length of approximately 10 mm.

14. In method of determining noninvasively and in vivo one or more unknown values of a known characteristic, including the steps of irradiating human tissue with at least one source of infrared energy having at least several wavelengths in a given range of wavelengths so that there is differential absorption of at least some of said wavelengths by said tissue as a function of said wavelengths and said characteristic, said differential absorption causing intensity variations of said wavelengths, collecting wilh at least one detector at least some of said wavelengths that have traversed an average optical path through said tissue, and calculating said one or more unknown values of said known characteristics, the improvement comprising: positioning said at least one source and said at least one detector relative to said tissue to provide at least first and second average optical paths through said tissue, said first path being different in length from said second path, one of said paths representing a partial transmission path which passes through the nail of a finger twice.

* * * * *